(12) United States Patent
Strasemeier et al.

(10) Patent No.: US 11,497,657 B2
(45) Date of Patent: Nov. 15, 2022

(54) ABSORBENT ARTICLES HAVING CHANNELS AND WETNESS INDICATOR

(71) Applicant: The Procter & Gamble Company, Cincinnati, OH (US)

(72) Inventors: John Andrew Strasemeier, Aurora, IN (US); Theodore Cory Fites, Cincinnati, OH (US); Sarah Ann Sanborn, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 368 days.

(21) Appl. No.: 16/690,330

(22) Filed: Nov. 21, 2019

(65) Prior Publication Data

US 2020/0085638 A1  Mar. 19, 2020

Related U.S. Application Data

(63) Continuation of application No. 15/162,642, filed on May 24, 2016, now Pat. No. 10,543,129.

(Continued)

(51) Int. Cl.
*A61F 13/42* (2006.01)
*A61F 13/532* (2006.01)
(Continued)

(52) U.S. Cl.
CPC .............. *A61F 13/42* (2013.01); *A61F 13/49* (2013.01); *A61F 13/49001* (2013.01);
(Continued)

(58) Field of Classification Search
CPC .... A61F 13/42; A61F 13/49; A61F 13/49001; A61F 13/51496; A61F 13/533; A61F 2013/422; A61F 2013/8497
See application file for complete search history.

(56) References Cited

U.S. PATENT DOCUMENTS 1,733,997 A  10/1929  Marr
1,734,499 A  11/1929  Marinsky
(Continued)

FOREIGN PATENT DOCUMENTS

CA  2001370  4/1990
CA  2291997  6/2000
(Continued)

OTHER PUBLICATIONS

All Office Actions; U.S. Appl. No. 15/162,642; See Pair.
(Continued)

*Primary Examiner* — Catharine L Anderson
(74) *Attorney, Agent, or Firm* — Christian M. Best; Sarah M. DeCristofaro

(57) ABSTRACT

An absorbent article, such as a diaper or a training pant, having a wearer-facing side and a garment-facing side and a longitudinal axis. The absorbent article comprises a topsheet on the wearer-facing side, a backsheet on the garment-facing side, and an absorbent core between the topsheet and backsheet. The absorbent core comprises a generally longitudinally-extending channel. The absorbent article further comprises a wetness indicator at least partially superposed with the channel, as seen from the garment-facing side of the article.

20 Claims, 7 Drawing Sheets

Related U.S. Application Data

(60) Provisional application No. 62/167,937, filed on May 29, 2015.

(51) Int. Cl.
    *A61F 13/49*         (2006.01)
    *A61F 13/514*       (2006.01)
    *A61F 13/84*        (2006.01)

(52) U.S. Cl.
    CPC ...... *A61F 13/51496* (2013.01); *A61F 13/532* (2013.01); *A61F 2013/422* (2013.01); *A61F 2013/427* (2013.01); *A61F 2013/428* (2013.01); *A61F 2013/8497* (2013.01)

(56) References Cited

U.S. PATENT DOCUMENTS

| | | |
|---|---|---|
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Morin |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Gustavo |
| 3,180,335 A | 4/1965 | Duncan et al. |
| 3,207,158 A | 9/1965 | Yoshitake et al. |
| 3,227,160 A | 1/1966 | Joy |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 10/1974 | Sabee |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr et al. |
| 4,469,710 A | 9/1984 | Rielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievet et al. |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola et al. |
| 4,578,072 A | 3/1986 | Lancaster |
| 4,578,702 A | 3/1986 | Campbell |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,646,510 A | 3/1987 | McIntyre |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| RE32,649 E | 4/1988 | Brandt et al. |
| 4,741,941 A | 5/1988 | Englebert et al. |
| 4,747,846 A | 5/1988 | Boland et al. |

(56) References Cited

U.S. PATENT DOCUMENTS

| | | |
|---|---|---|
| 4,753,648 A | 6/1988 | Jackson |
| 4,773,905 A | 9/1988 | Molee |
| 4,784,892 A | 11/1988 | Storey et al. |
| 4,785,996 A | 11/1988 | Ziecker et al. |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Fröidh et al. |
| 4,806,408 A | 2/1989 | Pierre et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak et al. |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki et al. |
| 4,892,535 A | 1/1990 | Bjornberg |
| 4,892,536 A | 1/1990 | DesMarais et al. |
| 4,894,060 A | 1/1990 | Nestegard |
| 4,894,277 A | 1/1990 | Akasaki |
| 4,904,251 A | 2/1990 | Igaue et al. |
| 4,900,317 A | 3/1990 | Buell |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 8/1991 | Elliott |
| 5,072,687 A | 12/1991 | Mitchell |
| 5,085,654 A | 2/1992 | Buell |
| 5,087,255 A | 2/1992 | Sims et al. |
| 5,089,548 A * | 2/1992 | Zimmel ............... A61F 13/42 604/361 |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,382,610 A | 1/1995 | Harada et al. |
| 5,387,207 A | 2/1995 | Dyer et al. |
| 5,387,208 A | 2/1995 | Ashton et al. |
| 5,387,209 A | 2/1995 | Yamamoto et al. |
| 5,389,095 A | 2/1995 | Suzuki |
| 5,397,316 A | 3/1995 | Lavon et al. |
| 5,397,317 A | 3/1995 | Thomas |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,429,630 A | 7/1995 | Beal et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,460,623 A | 10/1995 | Emenaker et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,559,335 A | 9/1996 | Zing et al. |
| 5,560,878 A | 10/1996 | Dragoo et al. |
| 5,562,634 A | 10/1996 | Flumene et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,575,783 A | 11/1996 | Clear et al. |
| 5,580,411 A | 12/1996 | Nease et al. |
| 5,584,829 A | 12/1996 | Lavash et al. |
| 5,586,979 A | 12/1996 | Thomas |

(56) References Cited

U.S. PATENT DOCUMENTS

| | | |
|---|---|---|
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | DiPalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |
| 5,625,222 A | 4/1997 | Yoneda et al. |
| 5,607,416 A | 5/1997 | Yamamoto et al. |
| 5,626,571 A | 5/1997 | Young et al. |
| 5,628,741 A | 5/1997 | Buell et al. |
| 5,628,845 A | 5/1997 | Murray et al. |
| 5,635,191 A | 6/1997 | Roe et al. |
| 5,635,271 A | 6/1997 | Zafiroglu |
| 5,637,106 A | 6/1997 | Mitchell |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman et al. |
| 5,674,215 A | 10/1997 | Ronnberg |
| 5,681,300 A | 10/1997 | Ahr |
| 5,683,374 A | 11/1997 | Yamamoto |
| 5,685,874 A | 11/1997 | Buell et al. |
| 5,690,624 A | 11/1997 | Sasaki et al. |
| 5,690,627 A | 11/1997 | Clear et al. |
| 5,691,035 A | 11/1997 | Chappell et al. |
| 5,691,036 A | 11/1997 | Chappell et al. |
| 5,695,488 A | 12/1997 | Sosalla |
| 5,700,254 A | 12/1997 | McDowall et al. |
| 5,702,376 A | 12/1997 | Glaug |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall et al. |
| H1732 H | 6/1998 | Johnson |
| 5,762,641 A | 6/1998 | Bewick Sonntag et al. |
| 5,766,388 A | 6/1998 | Pelley |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mitzutani |
| 5,855,572 A | 1/1999 | Schmidt |
| 5,858,013 A | 1/1999 | Kling |
| 5,858,515 A | 1/1999 | Stokes et al. |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,879,751 A | 3/1999 | Bogdanski |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,925,439 A | 7/1999 | Haubach |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,056,732 A | 5/2000 | Fujioka et al. |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,093,474 A | 7/2000 | Sironi |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,254,583 B1 | 7/2001 | Muhar |
| 6,258,996 B1 | 7/2001 | Goldman |

(56) References Cited

U.S. PATENT DOCUMENTS

| | | |
|---|---|---|
| 6,265,488 B1 | 7/2001 | Fujino et al. |
| 6,290,686 B1 | 9/2001 | Tanzer et al. |
| 6,306,122 B1 | 10/2001 | Narawa et al. |
| 6,315,765 B1 | 11/2001 | Datta |
| 6,319,239 B1 | 11/2001 | Daniels et al. |
| 6,322,552 B1 | 11/2001 | Blenke et al. |
| 6,325,787 B1 | 12/2001 | Roe et al. |
| 6,326,525 B1 | 12/2001 | Hamajima |
| 6,330,735 B1 | 12/2001 | Hahn et al. |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,402,731 B1 | 1/2002 | Suprise et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,403,857 B1 | 6/2002 | Gross et al. |
| 6,406,467 B1 | 6/2002 | Dilnik et al. |
| 6,409,883 B1 | 6/2002 | Makolin |
| 6,410,820 B1 | 6/2002 | McFall et al. |
| 6,410,822 B1 | 6/2002 | Mizutani |
| 6,402,729 B1 | 7/2002 | Boberg et al. |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Schaefer et al. |
| 6,461,342 B2 | 10/2002 | Tanji et al. |
| 6,461,343 B1 | 10/2002 | Schaefer et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Graef |
| 6,524,294 B1 | 2/2003 | Hilston et al. |
| 6,525,240 B1 | 2/2003 | Graef |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LaMahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,129 B2 | 3/2004 | Ando et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Roe et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B1 | 5/2004 | Graef |
| 6,790,798 B1 | 9/2004 | Suzuki et al. |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,878,647 B1 | 4/2005 | Rezai |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |
| 6,962,578 B1 | 11/2005 | Lavon |

(56) References Cited

U.S. PATENT DOCUMENTS

| | | |
|---|---|---|
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |
| 6,972,011 B2 | 12/2005 | Maeda et al. |
| 6,979,564 B2 | 12/2005 | Glucksmann et al. |
| 6,982,052 B2 | 1/2006 | Daniels et al. |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kinoshita et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu |
| 7,125,470 B2 | 10/2006 | Graef |
| 7,132,585 B2 | 11/2006 | Kudo |
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,163,528 B2 | 1/2007 | Christon et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,241,280 B2 | 7/2007 | Christen et al. |
| 7,250,481 B2 | 7/2007 | Jaworek et al. |
| 7,252,657 B2 | 8/2007 | Mishima |
| 7,265,258 B2 | 9/2007 | Hamilton |
| 7,270,651 B2 | 9/2007 | Adams et al. |
| 7,285,178 B2 | 10/2007 | Mischler et al. |
| RE39,919 E | 11/2007 | Dodge, II et al. |
| 7,306,582 B2 | 12/2007 | Adams et al. |
| 7,311,696 B2 | 12/2007 | Christen et al. |
| 7,311,968 B2 | 12/2007 | Ehrnsperger et al. |
| 7,312,372 B2 | 12/2007 | Miyama |
| 7,318,820 B2 | 1/2008 | LaVon et al. |
| 7,329,244 B2 | 2/2008 | Otsubo |
| 7,329,246 B2 | 2/2008 | Kinoshita |
| 7,335,810 B2 | 2/2008 | Yoshimasa et al. |
| 7,377,914 B2 | 5/2008 | LaVon |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima |
| 7,504,552 B2 | 3/2009 | Tamura |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi |
| 7,550,646 B2 | 6/2009 | Tamura |
| 7,563,257 B2 | 7/2009 | Nakajima |
| 7,588,561 B2 | 9/2009 | Kenmochi |
| 7,594,904 B2 | 9/2009 | Rosenfeld |
| 7,598,428 B2 | 10/2009 | Gustavsson et al. |
| 7,625,363 B2 | 12/2009 | Yoshimasa |
| 7,641,642 B2 | 1/2010 | Murai et al. |
| 7,648,490 B2 | 1/2010 | Kuroda |
| 7,652,111 B2 | 1/2010 | Hermeling et al. |
| 7,666,173 B2 | 2/2010 | Mishima |
| 7,666,174 B2 | 2/2010 | Kawakami et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld |
| 7,696,402 B2 | 4/2010 | Nishikawa |
| 7,708,725 B2 | 5/2010 | Tamagawa |
| 7,717,150 B2 | 5/2010 | Manabe |
| 7,718,844 B2 | 5/2010 | Olson |
| 7,722,587 B2 | 5/2010 | Suzuki et al. |
| 7,722,590 B2 | 5/2010 | Tsuji |
| 7,727,217 B2 | 6/2010 | Hancock-Cooke |
| 7,736,351 B2 | 6/2010 | Nigam |
| 7,737,324 B2 | 6/2010 | LaVon et al. |
| 7,744,576 B2 | 6/2010 | Busam et al. |
| 7,744,578 B2 | 6/2010 | Tanio et al. |
| 7,750,203 B2 | 7/2010 | Busam et al. |
| 7,754,822 B2 | 7/2010 | Daniel et al. |
| 7,754,940 B2 | 7/2010 | Brisebois |
| 7,759,540 B2 | 7/2010 | Litvay et al. |
| 7,763,004 B2 | 7/2010 | Beck |
| 7,767,875 B2 | 8/2010 | Olson |
| 7,767,876 B2 | 8/2010 | Davis et al. |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 | 11/2010 | Elfsberg et al. |
| 7,838,722 B2 | 11/2010 | Blessing et al. |
| 7,850,672 B2 | 12/2010 | Guidotti et al. |
| 7,851,667 B2 | 12/2010 | Becker et al. |
| 7,855,314 B2 | 12/2010 | Hanao |
| 7,857,797 B2 | 12/2010 | Kudo |
| 7,858,842 B2 | 12/2010 | Komatsu |
| 7,884,259 B2 | 2/2011 | Hanao |
| 7,888,549 B2 | 2/2011 | Jansson et al. |
| 7,910,797 B2 | 3/2011 | Nandrea |
| 7,931,636 B2 | 4/2011 | LaVon et al. |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur |
| 7,951,126 B2 | 5/2011 | Nanjyo |
| 7,959,620 B2 | 6/2011 | Miura et al. |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe |
| 8,124,828 B2 | 2/2012 | Kline et al. |
| 8,133,212 B2 | 3/2012 | Takada |
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda |
| 8,178,747 B2 | 5/2012 | Venturino et al. |
| 8,183,430 B2 | 5/2012 | Hakansson et al. |
| 8,186,296 B2 | 5/2012 | Brown et al. |
| 8,187,239 B2 | 5/2012 | LaVon et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama |
| 8,246,594 B2 | 8/2012 | Sperl |
| 8,258,367 B2 | 9/2012 | Lawson et al. |
| 8,268,424 B1 | 9/2012 | Suzuki |
| 8,273,943 B2 | 9/2012 | Noda |
| 8,282,617 B2 | 10/2012 | Kaneda |
| 8,283,516 B2 | 10/2012 | Litvay |
| 8,317,766 B2 | 11/2012 | Naoto |
| 8,317,768 B2 | 11/2012 | Larsson |
| 8,319,005 B2 | 11/2012 | Becker et al. |
| 8,343,123 B2 | 1/2013 | Noda |
| 8,343,296 B2 | 1/2013 | Blessing et al. |
| 8,360,977 B2 | 1/2013 | Marttila |

(56) References Cited

U.S. PATENT DOCUMENTS

| | | |
|---|---|---|
| 8,361,047 B2 | 1/2013 | Mukai |
| 8,377,025 B2 | 2/2013 | Nakajima |
| 8,450,555 B2 | 5/2013 | Nahn et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 | 10/2013 | Jackels et al. |
| 8,569,571 B2 | 10/2013 | Kline et al. |
| 8,581,019 B2 | 11/2013 | Carlucci et al. |
| 8,603,058 B2 | 12/2013 | Sprerl et al. |
| 8,604,270 B2 | 12/2013 | Venturino et al. |
| 8,633,347 B2 | 1/2014 | Bianco et al. |
| 8,664,468 B2 | 3/2014 | Lawson et al. |
| 8,674,170 B2 | 3/2014 | Busam et al. |
| 8,734,417 B2 | 5/2014 | LaVon et al. |
| 8,766,031 B2 | 7/2014 | Becker et al. |
| 8,772,570 B2 | 7/2014 | Kawakami et al. |
| 8,784,594 B2 | 7/2014 | Blessing et al. |
| 8,785,715 B2 | 7/2014 | Wright et al. |
| 8,791,318 B2 | 7/2014 | Becker et al. |
| 8,936,584 B2 | 1/2015 | Zander et al. |
| 9,056,034 B2 | 6/2015 | Akiyama |
| 9,326,896 B2 | 5/2016 | Schaefer et al. |
| 2001/0007065 A1 | 7/2001 | Blanchard |
| 2001/0008964 A1 | 7/2001 | Kurata et al. |
| 2001/0016548 A1 | 8/2001 | Kugler et al. |
| 2001/0020157 A1 | 9/2001 | Mizutani |
| 2001/0037101 A1 | 11/2001 | Allan et al. |
| 2001/0044610 A1 | 11/2001 | Kim |
| 2002/0007167 A1 | 1/2002 | Dan |
| 2002/0007169 A1 | 1/2002 | Graef et al. |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0062116 A1 | 5/2002 | Mizutani et al. |
| 2002/0065498 A1 | 5/2002 | Ohashi |
| 2002/0072471 A1 | 6/2002 | Ikeuchi et al. |
| 2002/0082575 A1 | 6/2002 | Dan |
| 2002/0087139 A1 | 7/2002 | Popp et al. |
| 2002/0095127 A1 | 7/2002 | Fish et al. |
| 2002/0102392 A1 | 8/2002 | Fish et al. |
| 2002/0115969 A1 | 8/2002 | Maeda et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |
| 2002/0016122 A1 | 12/2002 | Curro et al. |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0105190 A1 | 6/2003 | Diehl et al. |
| 2003/0109839 A1 | 6/2003 | Costae et al. |
| 2003/0114811 A1 | 6/2003 | Christen et al. |
| 2003/0114816 A1 | 6/2003 | Underhill |
| 2003/0114818 A1 | 6/2003 | Benecke et al. |
| 2003/0115969 A1 | 6/2003 | Koyano et al. |
| 2003/0120235 A1 | 6/2003 | Boulanger |
| 2003/0120249 A1 | 6/2003 | Wulz et al. |
| 2003/0233082 A1 | 6/2003 | Kline et al. |
| 2003/0135176 A1 | 7/2003 | Delzer et al. |
| 2003/0135181 A1 | 7/2003 | Chen et al. |
| 2003/0135182 A1 | 7/2003 | Woon et al. |
| 2003/0139712 A1 | 7/2003 | Dodge |
| 2003/0139715 A1 | 7/2003 | Dodge |
| 2003/0139718 A1 | 7/2003 | Graef |
| 2003/0144642 A1 | 7/2003 | Dopps |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0158530 A1 | 8/2003 | Diehl et al. |
| 2003/0158531 A1 | 8/2003 | Chmielewski |
| 2003/0158532 A1 | 8/2003 | Magee et al. |
| 2003/0167045 A1 | 9/2003 | Graef |
| 2003/0171727 A1 | 9/2003 | Graef |
| 2003/0208175 A1 | 11/2003 | Gross |
| 2003/0225385 A1 | 12/2003 | Glaug |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett |
| 2004/0063367 A1 | 4/2004 | Dodge |
| 2004/0064113 A1 | 4/2004 | Erdman |
| 2004/0064115 A1 | 4/2004 | Arora |
| 2004/0064116 A1 | 4/2004 | Arora |
| 2004/0064125 A1 | 4/2004 | Justmann et al. |
| 2004/0065420 A1 | 4/2004 | Graef |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127131 A1 | 7/2004 | Potnis |
| 2004/0127871 A1 | 7/2004 | Odorzynski |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0167489 A1 | 8/2004 | Kellenberger et al. |
| 2004/0170813 A1 | 9/2004 | Digiacomantonio et al. |
| 2004/0193127 A1 | 9/2004 | Hansson |
| 2004/0215160 A1 | 10/2004 | Chmielewski |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0249355 A1 | 12/2004 | Tanio et al. |
| 2004/0260259 A1 | 12/2004 | Baker |
| 2005/0001929 A1 | 1/2005 | Waksmundzki et al. |
| 2005/0004543 A1 | 1/2005 | Schroer |
| 2005/0004548 A1 | 1/2005 | Otsubo et al. |
| 2005/0008839 A1 | 1/2005 | Cramer et al. |
| 2005/0018258 A1 | 1/2005 | Miyagi |
| 2005/0038401 A1 | 2/2005 | Suzuki et al. |
| 2005/0070867 A1 | 3/2005 | Beruda et al. |
| 2005/0085784 A1 | 4/2005 | LeMinh et al. |
| 2005/0090789 A1 | 4/2005 | Graef |
| 2005/0101929 A1 | 5/2005 | Waksmundzki et al. |
| 2005/0137543 A1 | 6/2005 | Underhill et al. |
| 2005/0148258 A1 | 7/2005 | Chakravarty |
| 2005/0148961 A1 | 7/2005 | Sosalla et al. |
| 2005/0148990 A1 | 7/2005 | Shimoe |
| 2005/0154363 A1 | 7/2005 | Minato |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0217791 A1 | 10/2005 | Costello et al. |
| 2005/0229543 A1 | 10/2005 | Tippey |
| 2005/0234414 A1 | 10/2005 | Liu et al. |
| 2005/0245684 A1 | 11/2005 | Daniel et al. |
| 2005/0288645 A1 | 12/2005 | LaVon |
| 2005/0288646 A1 | 12/2005 | LaVon |
| 2006/0004334 A1 | 1/2006 | Schlinz et al. |
| 2006/0021695 A1 | 2/2006 | Blessing et al. |
| 2006/0024433 A1 | 2/2006 | Blessing et al. |
| 2006/0069367 A1 | 3/2006 | Waksmundzki et al. |
| 2006/0069371 A1 | 3/2006 | Ohashi et al. |
| 2006/0073969 A1 | 4/2006 | Torli et al. |
| 2006/0081348 A1 | 4/2006 | Graef |
| 2006/0129114 A1 | 6/2006 | Mason et al. |
| 2006/0142724 A1 | 6/2006 | Watanabe |
| 2006/0155057 A1 | 7/2006 | Hermeling et al. |

(56) References Cited

U.S. PATENT DOCUMENTS

| | | |
|---|---|---|
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley |
| 2006/0206091 A1 | 9/2006 | Cole |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | Lavon et al. |
| 2006/0271010 A1 | 11/2006 | LaVon et al. |
| 2007/0049892 A1 | 1/2007 | Lord et al. |
| 2007/0027436 A1 | 2/2007 | Nakagawa et al. |
| 2007/0032770 A1 | 2/2007 | Lavon et al. |
| 2007/0043191 A1 | 2/2007 | Hermeling et al. |
| 2007/0043330 A1 | 2/2007 | Lankhof et al. |
| 2007/0044903 A1 | 3/2007 | Wisneski et al. |
| 2007/0049897 A1 | 3/2007 | LaVon et al. |
| 2007/0073253 A1 | 3/2007 | Miyama |
| 2007/0078422 A1 | 4/2007 | Glaug |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug |
| 2007/0219521 A1 | 9/2007 | Hird et al. |
| 2007/0219523 A1 | 9/2007 | Bruun |
| 2007/0244455 A1 | 10/2007 | Hansson et al. |
| 2007/0246147 A1 | 10/2007 | Venturino et al. |
| 2007/0255245 A1 | 11/2007 | Asp et al. |
| 2007/0282288 A1 | 12/2007 | Noda |
| 2007/0282290 A1 | 12/2007 | Cole |
| 2007/0282291 A1 | 12/2007 | Cole |
| 2008/0027402 A1 | 1/2008 | Schmidt et al. |
| 2008/0091159 A1 | 4/2008 | Carlucci et al. |
| 2008/0119810 A1 | 5/2008 | Kuroda |
| 2008/0125735 A1 | 5/2008 | Busam et al. |
| 2008/0132864 A1 | 6/2008 | Lawson et al. |
| 2008/0208154 A1 | 8/2008 | Oetjen et al. |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto |
| 2008/0268194 A1 | 10/2008 | Kim et al. |
| 2008/0274227 A1 | 11/2008 | Boatman et al. |
| 2008/0281287 A1 | 11/2008 | Marcelo |
| 2008/0294140 A1 | 11/2008 | Ecker et al. |
| 2008/0032035 A1 | 12/2008 | Schmidt et al. |
| 2008/0312617 A1 | 12/2008 | Hundorf et al. |
| 2008/0312618 A1 | 12/2008 | Hundorf et al. |
| 2008/0312619 A1 | 12/2008 | Hundorf et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0062760 A1 | 3/2009 | Wright et al. |
| 2009/0112173 A1 | 4/2009 | Bissah |
| 2009/0112175 A1 | 4/2009 | Bissah et al. |
| 2009/0157022 A1 | 6/2009 | Macdonald |
| 2009/0192035 A1 | 7/2009 | Stueven et al. |
| 2009/0240220 A1 | 9/2009 | Macdonald |
| 2009/0058994 A1 | 10/2009 | Stueven et al. |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo |
| 2009/0318884 A1 | 12/2009 | Meyer et al. |
| 2009/0326494 A1 | 12/2009 | Uchida et al. |
| 2010/0051166 A1 | 3/2010 | Hundorf et al. |
| 2010/0062165 A1 | 3/2010 | Suzuki |
| 2010/0062934 A1 | 3/2010 | Suzuki |
| 2010/0063470 A1 | 3/2010 | Suzuki |
| 2010/0068520 A1 | 3/2010 | Stueven et al. |
| 2010/0100065 A1 | 4/2010 | Bianco |
| 2010/0115237 A1 | 5/2010 | Brewer et al. |
| 2010/0121296 A1 | 5/2010 | Noda |
| 2010/0137773 A1 | 6/2010 | Gross |
| 2010/0137823 A1 | 6/2010 | Corneliusson |
| 2010/0198179 A1 | 8/2010 | Noda |
| 2010/0228210 A1 | 9/2010 | Busam et al. |
| 2010/0241096 A1 | 9/2010 | LaVon et al. |
| 2010/0241097 A1 | 9/2010 | Nigam et al. |
| 2010/0262099 A1 | 10/2010 | Klofta |
| 2010/0262104 A1 | 10/2010 | Carlucci et al. |
| 2010/0274208 A1 | 10/2010 | Gabrielii |
| 2010/0274210 A1 | 10/2010 | Noda |
| 2010/0312208 A1 | 12/2010 | Bond et al. |
| 2010/0324521 A1 | 12/2010 | Mukai |
| 2010/0324523 A1 | 12/2010 | Mukai |
| 2011/0041999 A1 | 2/2011 | Hundorf et al. |
| 2011/0060301 A1 | 3/2011 | Nishikawa et al. |
| 2011/0060303 A1 | 3/2011 | Bissah |
| 2011/0066127 A1 | 3/2011 | Kuwano |
| 2011/0071486 A1 | 3/2011 | Harada |
| 2011/0092944 A1 | 4/2011 | Sagisaka |
| 2011/0112498 A1 | 5/2011 | Nhan et al. |
| 2011/0125120 A1 | 5/2011 | Nishitani |
| 2011/0130732 A1 | 6/2011 | Jackels et al. |
| 2011/0130737 A1 | 6/2011 | Sagisaka |
| 2011/0137276 A1 | 6/2011 | Yoshikawa |
| 2011/0144602 A1 | 6/2011 | Long |
| 2011/0144604 A1 | 6/2011 | Noda |
| 2011/0144606 A1 | 6/2011 | Nandrea |
| 2011/0152813 A1 | 6/2011 | Ellingson |
| 2011/0166540 A1 | 7/2011 | Yang et al. |
| 2011/0172630 A1 | 7/2011 | Nomoto |
| 2011/0174430 A1 | 7/2011 | Zhao |
| 2011/0196330 A1 | 8/2011 | Hammons et al. |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda |
| 2011/0295222 A1 | 12/2011 | Becker et al. |
| 2011/0319846 A1 | 12/2011 | Rinnert et al. |
| 2011/0319848 A1 | 12/2011 | McKiernan et al. |
| 2011/0319851 A1 | 12/2011 | Kudo |
| 2012/0004633 A1 | 1/2012 | R Marcelo |
| 2012/0016326 A1 | 1/2012 | Brennan et al. |
| 2012/0022479 A1 | 1/2012 | Cotton |
| 2012/0035566 A1 | 2/2012 | Sagisaka |
| 2012/0035576 A1 | 2/2012 | Ichikawa |
| 2012/0064792 A1 | 3/2012 | Bauduin |
| 2012/0071848 A1 | 3/2012 | Zhang |
| 2012/0089106 A1 | 4/2012 | Komatsu |
| 2012/0165771 A1 | 6/2012 | Ruman et al. |
| 2012/0165776 A1 | 6/2012 | Rinnert et al. |
| 2012/0175056 A1 | 7/2012 | Tsang |
| 2012/0184934 A1 | 7/2012 | Venturino |
| 2012/0232514 A1 | 9/2012 | Baker |
| 2012/0238977 A1 | 9/2012 | Oku |
| 2012/0253306 A1 | 10/2012 | Otsubo |
| 2012/0256750 A1 | 10/2012 | Novak |
| 2012/0271262 A1 | 10/2012 | Venturino |
| 2012/0170779 A1 | 12/2012 | Rosati et al. |

(56) References Cited

U.S. PATENT DOCUMENTS

| | | |
|---|---|---|
| 2012/0312491 A1 | 12/2012 | Jackels et al. |
| 2012/0316046 A1 | 12/2012 | Jackels et al. |
| 2012/0316523 A1 | 12/2012 | Hippe et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah |
| 2012/0323202 A1 | 12/2012 | Bissah |
| 2013/0035656 A1 | 2/2013 | Moriya et al. |
| 2013/0041334 A1 | 2/2013 | Prioleau |
| 2013/0178811 A1 | 7/2013 | Kikuchi et al. |
| 2013/0211354 A1 | 8/2013 | Tsuji et al. |
| 2013/0211358 A1 | 8/2013 | Kikkawa et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2013/0310784 A1 | 11/2013 | Bryant et al. |
| 2014/0005622 A1 | 1/2014 | Wirtz et al. |
| 2014/0005623 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0102183 A1 | 4/2014 | Agami et al. |
| 2014/0121623 A1 | 5/2014 | Kirby et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0171893 A1 | 6/2014 | Lawson et al. |
| 2014/0318694 A1 | 10/2014 | Blessing et al. |
| 2014/0324007 A1 | 10/2014 | Hundorf et al. |
| 2014/0324008 A1 | 10/2014 | Hundorf et al. |
| 2015/0065973 A1 | 3/2015 | Roe et al. |
| 2015/0065976 A1 | 3/2015 | Roe et al. |
| 2015/0065981 A1 | 3/2015 | Roe et al. |
| 2015/0065986 A1 | 3/2015 | Blessing et al. |
| 2015/0080837 A1 | 3/2015 | Rosati et al. |
| 2015/0080839 A1 | 3/2015 | Tapp et al. |
| 2015/0173967 A1 | 6/2015 | Kreuzer et al. |
| 2015/0173968 A1 | 6/2015 | Joseph |
| 2015/0250662 A1 | 9/2015 | Isele et al. |
| 2016/0346136 A1 | 12/2016 | Strasemeier et al. |
| 2017/0128275 A1 | 5/2017 | Tanio |
| 2017/0165123 A1 | 6/2017 | Gogin |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 1371671 | 2/2001 |
| CN | 2527254 Y | 12/2002 |
| CN | 2535020 Y | 2/2003 |
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 3205931 C2 | 9/1983 |
| DE | 3608114 A1 | 9/1987 |
| DE | 19732499 | 2/1999 |
| DE | 10204937 A1 | 8/2003 |
| EP | 083022 | 7/1983 |
| EP | 149880 | 7/1985 |
| EP | 0149880 A2 | 7/1985 |
| EP | 203289 | 12/1986 |
| EP | 0203289 A2 | 12/1986 |
| EP | 0206208 | 12/1986 |
| EP | 209561 B1 | 1/1987 |
| EP | 297411 B1 | 1/1989 |
| EP | 304957 | 3/1989 |
| EP | 374542 | 6/1990 |
| EP | 394274 | 10/1990 |
| EP | 0403832 | 12/1990 |
| EP | 481322 B1 | 4/1992 |
| EP | 530438 | 3/1993 |
| EP | 547847 | 6/1993 |
| EP | 555346 | 8/1993 |
| EP | 559476 | 9/1993 |
| EP | 591647 B2 | 4/1994 |
| EP | 597273 B1 | 5/1994 |
| EP | 601610 B2 | 6/1994 |
| EP | 632068 | 1/1995 |
| EP | 0640330 A1 | 3/1995 |
| EP | 0668066 | 9/1995 |
| EP | 685214 | 12/1995 |
| EP | 687453 | 12/1995 |
| EP | 0689817 | 1/1996 |
| EP | 0691133 | 1/1996 |
| EP | 0700673 | 3/1996 |
| EP | 0394274 | 7/1996 |
| EP | 724418 | 8/1996 |
| EP | 725613 | 8/1996 |
| EP | 725615 | 8/1996 |
| EP | 725616 | 8/1996 |
| EP | 758543 | 2/1997 |
| EP | 0761194 | 3/1997 |
| EP | 769284 | 4/1997 |
| EP | 0776645 A1 | 6/1997 |
| EP | 0781537 | 7/1997 |
| EP | 783877 B1 | 7/1997 |
| EP | 787472 | 8/1997 |
| EP | 788874 B1 | 8/1997 |
| EP | 796068 | 9/1997 |
| EP | 799004 | 10/1997 |
| EP | 822794 B1 | 2/1998 |
| EP | 826351 | 3/1998 |
| EP | 844861 | 6/1998 |
| EP | 0737055 | 8/1998 |
| EP | 863733 | 9/1998 |
| EP | 971751 | 9/1998 |
| EP | 0875224 | 11/1998 |
| EP | 875224 A1 | 11/1998 |
| EP | 880955 | 12/1998 |
| EP | 891758 | 1/1999 |
| EP | 0893115 | 1/1999 |
| EP | 0724418 | 3/1999 |
| EP | 0725613 | 3/1999 |
| EP | 0725616 | 3/1999 |
| EP | 904755 | 3/1999 |
| EP | 0916327 | 5/1999 |
| EP | 925769 A2 | 6/1999 |
| EP | 933074 | 8/1999 |
| EP | 937736 | 8/1999 |
| EP | 941157 | 9/1999 |
| EP | 947549 | 10/1999 |
| EP | 951887 B1 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 B1 | 3/2000 |
| EP | 0778762 | 4/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |

(56) References Cited

FOREIGN PATENT DOCUMENTS

| | | |
|---|---|---|
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 0796068 | 5/2001 |
| EP | 752892 | 7/2001 |
| EP | 1116479 A2 | 7/2001 |
| EP | 0790839 | 8/2001 |
| EP | 1132069 | 9/2001 |
| EP | 1173128 | 1/2002 |
| EP | 1175194 B1 | 1/2002 |
| EP | 1184018 | 3/2002 |
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1253231 | 10/2002 |
| EP | 1262531 A1 | 12/2002 |
| EP | 1263374 B1 | 12/2002 |
| EP | 0737056 | 1/2003 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 | 8/2004 |
| EP | 1447067 | 8/2004 |
| EP | 1460987 | 9/2004 |
| EP | 963749 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1621166 | 2/2006 |
| EP | 1621167 | 2/2006 |
| EP | 1632206 | 3/2006 |
| EP | 1642556 | 4/2006 |
| EP | 1403419 | 5/2006 |
| EP | 1656162 | 5/2006 |
| EP | 1669046 | 6/2006 |
| EP | 1688114 | 8/2006 |
| EP | 2314265 | 8/2006 |
| EP | 1723939 | 11/2006 |
| EP | 1738727 | 1/2007 |
| EP | 1754461 | 2/2007 |
| EP | 1787611 | 5/2007 |
| EP | 1813238 | 8/2007 |
| EP | 2008626 | 12/2008 |
| EP | 2055279 A1 | 5/2009 |
| EP | 2093049 | 8/2009 |
| EP | 2130522 | 12/2009 |
| EP | 1621165 | 4/2010 |
| EP | 2444046 | 4/2012 |
| EP | 2532328 | 12/2012 |
| EP | 2532329 A1 | 12/2012 |
| EP | 2532332 A1 | 12/2012 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| FR | 2566631 | 1/1986 |
| FR | 2583377 | 12/1986 |
| FR | 2612770 | 9/1988 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/KOL/1999 | 10/2005 |
| IN | 212479 B | 3/2007 |
| IN | 208543 B | 8/2007 |
| IN | 0980/MUM/2009 | 6/2009 |
| JP | 5572928 U | 5/1980 |
| JP | 598322 U | 1/1984 |
| JP | 630148323 U | 9/1988 |
| JP | 2107250 | 4/1990 |
| JP | 03224481 B2 | 10/1991 |
| JP | 04122256 | 4/1992 |
| JP | 04341368 | 11/1992 |
| JP | 06191505 | 7/1994 |
| JP | 06269475 A | 9/1994 |
| JP | 07124193 | 5/1995 |
| JP | 08215629 | 8/1996 |
| JP | H10295728 | 11/1998 |
| JP | 10328232 | 12/1998 |
| JP | 11033056 A | 2/1999 |
| JP | 11318980 | 11/1999 |
| JP | 11320742 | 11/1999 |
| JP | 2000232985 | 8/2000 |
| JP | 2000238161 | 9/2000 |
| JP | 2001037810 | 2/2001 |
| JP | 2001046435 A | 2/2001 |
| JP | 2001120597 | 5/2001 |
| JP | 2001158074 | 6/2001 |
| JP | 2001178768 A | 7/2001 |
| JP | 2001198157 | 7/2001 |
| JP | 2001224626 A | 8/2001 |
| JP | 2001277394 | 10/2001 |
| JP | 03420481 B2 | 11/2001 |
| JP | 2001321397 | 11/2001 |
| JP | 2001353174 A | 12/2001 |
| JP | 2002052042 A | 2/2002 |
| JP | 2002065718 | 3/2002 |
| JP | 2002113800 A | 4/2002 |
| JP | 2002165832 | 6/2002 |
| JP | 2002165836 | 6/2002 |
| JP | 2002178429 | 6/2002 |
| JP | 2002272769 A | 9/2002 |
| JP | 2002320641 | 11/2002 |
| JP | 2002325792 A | 11/2002 |
| JP | 2002325799 A | 11/2002 |
| JP | 2002369841 A | 12/2002 |
| JP | 2003126140 | 5/2003 |
| JP | 2003153955 A | 5/2003 |
| JP | 2003265523 | 9/2003 |
| JP | 2003265524 A | 9/2003 |
| JP | 2003275237 | 9/2003 |
| JP | 2003325563 | 11/2003 |
| JP | 2004089269 | 3/2004 |
| JP | 03566012 B2 | 6/2004 |
| JP | 03568146 B2 | 6/2004 |
| JP | 03616077 B2 | 11/2004 |
| JP | 2004337314 A | 12/2004 |
| JP | 2004337385 A | 12/2004 |
| JP | 2004350864 | 12/2004 |
| JP | 03640475 B2 | 1/2005 |
| JP | 2005000312 A | 1/2005 |

(56) References Cited

FOREIGN PATENT DOCUMENTS

| | | |
|---|---|---|
| JP | 03660816 B2 | 3/2005 |
| JP | 03676219 B2 | 5/2005 |
| JP | 03688403 B2 | 6/2005 |
| JP | 03705943 B2 | 8/2005 |
| JP | 03719819 B2 | 9/2005 |
| JP | 03724963 B2 | 9/2005 |
| JP | 03725008 B2 | 9/2005 |
| JP | 03737376 B2 | 11/2005 |
| JP | 2006014792 A | 1/2006 |
| JP | 03781617 B2 | 3/2006 |
| JP | 2006110329 | 4/2006 |
| JP | 2006513824 T | 4/2006 |
| JP | 03801449 B2 | 5/2006 |
| JP | 2006116036 A | 5/2006 |
| JP | 03850102 B2 | 9/2006 |
| JP | 03850207 B2 | 9/2006 |
| JP | 03856941 B2 | 9/2006 |
| JP | 03868628 B2 | 10/2006 |
| JP | 03874499 B2 | 11/2006 |
| JP | 03877702 B2 | 11/2006 |
| JP | 2006325639 A | 12/2006 |
| JP | 2006346021 | 12/2006 |
| JP | 03904356 B2 | 1/2007 |
| JP | 2007007455 A | 1/2007 |
| JP | 2007007456 A | 1/2007 |
| JP | 03926042 B2 | 3/2007 |
| JP | 03934855 B2 | 3/2007 |
| JP | 2007089906 A | 4/2007 |
| JP | 2007105198 A | 4/2007 |
| JP | 2007152033 A | 6/2007 |
| JP | 03986210 B2 | 7/2007 |
| JP | 03986222 B2 | 7/2007 |
| JP | 2007167453 | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 B2 | 11/2007 |
| JP | 04058281 B2 | 12/2007 |
| JP | 04061086 B2 | 12/2007 |
| JP | 04092319 B2 | 3/2008 |
| JP | 2008080150 A | 4/2008 |
| JP | 2008093289 A | 4/2008 |
| JP | 04124322 B2 | 5/2008 |
| JP | 2008119081 A | 5/2008 |
| JP | 2008136739 A | 6/2008 |
| JP | 2008136877 A | 6/2008 |
| JP | 04148594 B2 | 7/2008 |
| JP | 04148620 B2 | 7/2008 |
| JP | 2008154606 A | 7/2008 |
| JP | 04162609 B2 | 8/2008 |
| JP | 04162637 B2 | 8/2008 |
| JP | 04166923 B2 | 8/2008 |
| JP | 04167406 B2 | 8/2008 |
| JP | 04173723 B2 | 8/2008 |
| JP | 04190675 B2 | 9/2008 |
| JP | 04190693 B2 | 9/2008 |
| JP | 04208338 B2 | 10/2008 |
| JP | 2008246089 | 10/2008 |
| JP | 4177770 B2 | 11/2008 |
| JP | 04230971 B2 | 12/2008 |
| JP | 2008295475 A | 12/2008 |
| JP | 2008295713 A | 12/2008 |
| JP | 04261593 B2 | 2/2009 |
| JP | 2009112590 | 5/2009 |
| JP | 04322228 B2 | 6/2009 |
| JP | 2009136601 | 6/2009 |
| JP | 2009142401 A | 7/2009 |
| JP | 2009201878 A | 9/2009 |
| JP | 04392936 B2 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 | 1/2010 |
| JP | 04458702 B2 | 2/2010 |
| JP | 04459013 B2 | 2/2010 |
| JP | 2010022560 | 2/2010 |
| JP | 04481325 B2 | 3/2010 |
| JP | 2010051654 A | 3/2010 |
| JP | 2010063814 A | 3/2010 |
| JP | 2010063944 A | 3/2010 |
| JP | 04492957 B2 | 4/2010 |
| JP | 2010068954 A | 4/2010 |
| JP | 2010075462 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 | 6/2010 |
| JP | 2010131297 A | 6/2010 |
| JP | 2010136917 A | 6/2010 |
| JP | 2010136973 A | 6/2010 |
| JP | 04540563 B2 | 7/2010 |
| JP | 04587947 B2 | 9/2010 |
| JP | 2010194124 A | 9/2010 |
| JP | 2010201093 | 9/2010 |
| JP | 2010207457 | 9/2010 |
| JP | 2010221067 | 10/2010 |
| JP | 4577766 B2 | 11/2010 |
| JP | 04620299 B2 | 11/2010 |
| JP | 04627472 B2 | 11/2010 |
| JP | 04627473 B2 | 11/2010 |
| JP | 04638087 B2 | 12/2010 |
| JP | 04652626 B2 | 12/2010 |
| JP | 2010273842 A | 12/2010 |
| JP | 2010284418 A | 12/2010 |
| JP | 2011000480 A | 1/2011 |
| JP | 2011030700 | 2/2011 |
| JP | 04693574 B2 | 3/2011 |
| JP | 2011067484 A | 4/2011 |
| JP | 2011072720 A | 4/2011 |
| JP | 2011104014 | 6/2011 |
| JP | 2011104122 A | 6/2011 |
| JP | 2011120661 A | 6/2011 |
| JP | 2011125360 A | 6/2011 |
| JP | 2011125537 | 6/2011 |
| JP | 04776516 B2 | 7/2011 |
| JP | 2011130797 A | 7/2011 |
| JP | 2011130799 A | 7/2011 |
| JP | 2011156032 A | 8/2011 |
| JP | 2011156070 A | 8/2011 |
| JP | 2011156254 | 8/2011 |
| JP | 04824882 B2 | 9/2011 |
| JP | 4850272 B2 | 10/2011 |
| JP | 04855533 B2 | 11/2011 |
| JP | 2011239858 | 12/2011 |
| JP | 04931572 B2 | 2/2012 |
| JP | 04937225 B2 | 3/2012 |
| JP | 04953618 B2 | 3/2012 |
| JP | 04969437 B2 | 4/2012 |
| JP | 04969640 B2 | 4/2012 |
| JP | 4971491 B2 | 4/2012 |
| JP | 04974524 B2 | 4/2012 |
| JP | 04979780 B2 | 4/2012 |
| JP | 05016020 B2 | 6/2012 |
| JP | 05027364 B2 | 6/2012 |
| JP | 2012115378 | 6/2012 |
| JP | 05031082 B2 | 7/2012 |
| JP | 05042351 B2 | 7/2012 |
| JP | 05043569 B2 | 7/2012 |
| JP | 05043591 B2 | 7/2012 |
| JP | 05046488 B2 | 7/2012 |
| JP | 2012125452 | 7/2012 |
| JP | 2012125625 A | 7/2012 |
| JP | 05053765 B2 | 8/2012 |
| JP | 05070275 B2 | 8/2012 |
| JP | 05079931 B1 | 9/2012 |
| JP | 05080189 B2 | 9/2012 |

(56) References Cited

FOREIGN PATENT DOCUMENTS

| | | |
|---|---|---|
| JP | 05084442 B2 | 9/2012 |
| JP | 05084476 B2 | 9/2012 |
| JP | 5085770 B2 | 9/2012 |
| JP | 05089269 B2 | 9/2012 |
| JP | 2012179286 | 9/2012 |
| JP | 05113146 B2 | 10/2012 |
| JP | 05129536 B2 | 11/2012 |
| JP | 05105884 B2 | 12/2012 |
| JP | 5715806 B2 | 5/2015 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO9015830 | 12/1990 |
| WO | WO9219198 | 11/1992 |
| WO | WO9321237 | 10/1993 |
| WO | WO9321879 | 11/1993 |
| WO | WO9510996 | 4/1995 |
| WO | WO9511652 | 5/1995 |
| WO | WO9514453 | 6/1995 |
| WO | WO9515139 | 6/1995 |
| WO | WO9516424 | 6/1995 |
| WO | WO9516746 | 6/1995 |
| WO | WO9519753 | 7/1995 |
| WO | WO9521596 | 8/1995 |
| WO | WO9524173 | 9/1995 |
| WO | WO9526209 | 10/1995 |
| WO | WO9529657 | 11/1995 |
| WO | WO9532698 | 12/1995 |
| WO | WO9534329 | 12/1995 |
| WO | WO9616624 | 6/1996 |
| WO | WO9619173 | 6/1996 |
| WO | WO96029967 | 10/1996 |
| WO | WO9711659 | 4/1997 |
| WO | WO9717922 | 5/1997 |
| WO | WO 9724096 | 7/1997 |
| WO | WO9816179 | 4/1998 |
| WO | WO9816180 | 4/1998 |
| WO | WO9843684 | 10/1998 |
| WO | WO9913813 | 3/1999 |
| WO | WO9934841 | 7/1999 |
| WO | WO9951178 | 10/1999 |
| WO | WO200000235 | 1/2000 |
| WO | WO200032145 | 6/2000 |
| WO | WO200059430 | 10/2000 |
| WO | WO200115647 | 3/2001 |
| WO | WO200126596 | 4/2001 |
| WO | WO 0135886 | 5/2001 |
| WO | WO200207663 | 1/2002 |
| WO | WO200232962 | 4/2002 |
| WO | WO2002064877 | 8/2002 |
| WO | WO2002067809 | 9/2002 |
| WO | WO2003009794 | 2/2003 |
| WO | WO2003039402 | 5/2003 |
| WO | WO2003053297 | 7/2003 |
| WO | WO03079946 | 10/2003 |
| WO | WO03101622 | 12/2003 |
| WO | WO2003105738 | 12/2003 |
| WO | WO2004021946 | 3/2004 |
| WO | WO2004049995 | 6/2004 |
| WO | WO2004071539 | 8/2004 |
| WO | WO2004084784 | 10/2004 |
| WO | WO2004105664 | 12/2004 |
| WO | WO2005/018694 | 3/2005 |
| WO | WO2005087164 | 9/2005 |
| WO | WO2005/102237 | 11/2005 |
| WO | WO2006104024 | 5/2006 |
| WO | WO2006059922 | 6/2006 |
| WO | WO2006062258 | 6/2006 |
| WO | WO2006066029 | 6/2006 |
| WO | WO2006083584 | 8/2006 |
| WO | WO2006134904 | 12/2006 |
| WO | WO2006134906 | 12/2006 |
| WO | WO2007000315 | 1/2007 |
| WO | WO2007046052 | 4/2007 |
| WO | WO2007047598 | 4/2007 |
| WO | WO2007049725 | 5/2007 |
| WO | WO2007061035 | 5/2007 |
| WO | WO2007141744 | 12/2007 |
| WO | WO2007142145 | 12/2007 |
| WO | WO2007148502 | 12/2007 |
| WO | WO2008018922 | 2/2008 |
| WO | WO2008065945 | 6/2008 |
| WO | WO2008146749 | 12/2008 |
| WO | WO2008155699 | 12/2008 |
| WO | WO2009004941 | 1/2009 |
| WO | WO2009005431 | 1/2009 |
| WO | WO2009139248 | 1/2009 |
| WO | WO2009139255 | 1/2009 |
| WO | WO2009041223 | 4/2009 |
| WO | WO2009096108 | 8/2009 |
| WO | WO2009107435 | 9/2009 |
| WO | WO2009122830 | 10/2009 |
| WO | WO2009152018 | 12/2009 |
| WO | WO2009155264 | 12/2009 |
| WO | WO2009155265 | 12/2009 |
| WO | WO2010071508 | 6/2010 |
| WO | WO2010074319 | 7/2010 |
| WO | WO2010107096 | 9/2010 |
| WO | WO2010114052 | 10/2010 |
| WO | WO2010117015 | 10/2010 |
| WO | WO2010118272 | 10/2010 |
| WO | WO201153044 | 5/2011 |
| WO | WO2011118725 | 9/2011 |
| WO | WO2011118842 | 9/2011 |
| WO | WO2011145653 | 11/2011 |
| WO | WO2011150955 | 12/2011 |
| WO | WO2011163582 | 12/2011 |
| WO | WO2012002252 | 1/2012 |
| WO | WO2012014436 | 2/2012 |
| WO | WO2012042908 | 4/2012 |
| WO | WO2012043077 | 4/2012 |
| WO | WO2012043078 | 4/2012 |
| WO | WO2012052172 | 4/2012 |
| WO | WO2012043082 | 5/2012 |
| WO | WO2012067216 | 5/2012 |
| WO | WO2012073499 | 6/2012 |
| WO | WO2012074466 | 6/2012 |
| WO | WO201291016 | 7/2012 |
| WO | WO2012090508 | 7/2012 |
| WO | WO2012101934 | 8/2012 |
| WO | WO2012102034 | 8/2012 |
| WO | WO2012117764 | 9/2012 |
| WO | WO2012117824 | 9/2012 |
| WO | WO2012132460 | 10/2012 |
| WO | WO2012170778 | 12/2012 |
| WO | WO2012170779 | 12/2012 |
| WO | WO2012170781 | 12/2012 |
| WO | WO2012170808 | 12/2012 |
| WO | WO2012174026 | 12/2012 |
| WO | WO2012177400 | 12/2012 |
| WO | WO2013001788 | 1/2013 |
| WO | WO2013046701 | 4/2013 |
| WO | WO2013060733 | 5/2013 |
| WO | WO2014073636 | 5/2014 |
| WO | WO2014078247 | 5/2014 |

OTHER PUBLICATIONS

International Search Report and Written Opinion; Application Ser. No. PCT/US2016/033855; dated Aug. 8, 2016, 12 pages.
PubChem Compound Summary—Bromophenol Blue, Mar. 26, 2005, Section 3.2.3 Solubility (Year: 2005).

* cited by examiner

ABSORBENT ARTICLES HAVING CHANNELS AND WETNESS INDICATOR

FIELD OF THE INVENTION

The invention is directed at absorbent articles for personal hygiene that are worn in the crotch region of the wearer, for example baby diapers, training pants and adult incontinence products. The articles comprise channels and a wetness indicator.

BACKGROUND OF THE INVENTION

Absorbent articles for personal hygiene of the type indicated above are designed to absorb and contain body exudates, in particular large quantity of urine. These absorbent articles comprise several layers, for example a topsheet, a backsheet and in-between an absorbent core, among other layers. The function of the absorbent core is to absorb and retain the exudates for a prolonged amount of time, minimize re-wet to keep the wearer dry and avoid soiling of clothes or bed sheets. The majority of absorbent cores comprise an absorbent material within a core wrap. A first type of commonly used absorbent material is a blend of comminuted wood pulp (so-called "air-felt") with superabsorbent polymers (SAP) in particulate form, also called absorbent gelling materials (AGM). Another type of cores having SAP as absorbent material without cellulose fibers (so called "airfelt-free" cores) has been more recently proposed.

Fluid-distributing channels extending longitudinally have been proposed for both types of cores. The channels can distribute an insulting fluid quickly along a greater area of the absorbent core thus improving fluid acquisition and optimizing absorbent material usage. Channels may also be used to facilitate the folding of the absorbent core in a pre-determined fashion, thus improving the anatomical conformity of the article. Various channel designs have thus been suggested. In air-felt cores, channels may be provided for example by locally embossing the absorbent material. Channels may also be provided by zones substantially free of absorbent material and surrounded by absorbent material. The top layer of core wrap may be attached to the bottom layer of the core wrap through these areas substantially free of absorbent material by a core wrap bond (herein "channel bond"), so that the channels are more resilient to the movement of the wearer or the swelling of the core with a fluid. The core wrap typically comprises one or two layers of a nonwoven synthetic material, typically PP or PE. The channel bonds may be provided by various means such as gluing, pressure, heat and/or ultrasonic bonding of the core wrap. On the other hand, it is simpler and less costly for the manufacturer to not bond the core wrap through the channels. The presence of channels in an absorbent core can be difficult to recognize before use because modern absorbent articles can be very thin. WO2015/039062 suggests creating a signal to highlight the channels for example by printing a printed adhesive layer between the topsheet and the absorbent core. WO2012/014436A1 discloses a disposable absorbent article having a display area adapted to be visually recognized from both an inner side and an outer side of the article. The liquid absorbent structure is formed with central void and lateral voids. The display area can be visually recognized from the garment-facing side through the central void. The display area may comprise a urine indicator.

SUMMARY OF THE INVENTION

The present invention is for an absorbent article, such as a diaper or a training pant, as indicated in the claims. The absorbent article of the invention has a wearer-facing side and a garment-facing side and comprises:
a topsheet on the wearer-facing side,
a backsheet on the garment-facing side, and
an absorbent core between the topsheet and backsheet.

The absorbent core comprises a core wrap having a top layer and a bottom layer enclosing an absorbent material and a generally longitudinally-extending channel. The article further comprises a wetness indicator at least partially superposed with the channel, as seen from the garment-facing side of the article.

By advantageously placing the wetness indicator at least partially within the area defined by the channel as seen from the exterior of the article, two key features are provided: first, the wetness indicator can react more quickly after a fluid insult's, communicating at an early stage to the caregiver that the diaper has been wetted. The channel allows quicker access for the fluid thereby triggering more quickly the wetness indicator. Second, it is often not recognizable for the user when a dry diaper comprises channels in the absorbent core. Placing the wetness indicator within the area of the channel (as seen from the outside of the article) provide a signal to the user that the product has the channels technology and can provide a signal relative to the size and placements of the channel within the article.

DETAILED DESCRIPTION OF THE INVENTION

Introduction

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

As used herein, the term "wearer" refers to an incontinent person, which may be an adult, child, or baby, and that will wear the absorbent product. The term "user" refers to the caregiver that applies the absorbent article on the wearer. The "user" may be a parent, a family member in general or a professionally employed caregiver.

The invention will now be further illustrated with reference to the embodiments as described in the Figures. For ease of discussion, absorbent articles and their components such as the absorbent core will be discussed with reference to the numerals referred to in these Figures. However it should be understood that these exemplary embodiments and the numerals are not intended to limit the scope of the claims, unless specifically indicated. Dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

General Description of the Article 20

As used herein, the term "absorbent articles" refers to disposable products for personal hygiene such as baby diapers, infant training pants or adult incontinence products and the like which are placed against or in proximity to the body of the wearer to absorb and contain exudates discharged from the body, in particular urine. The absorbent articles of the invention will be further illustrated in the below description and in the Figures in the form of a taped diaper. Nothing in this description should be however considered limiting the scope of the claims unless explicitly indicated otherwise.

Figure 1:
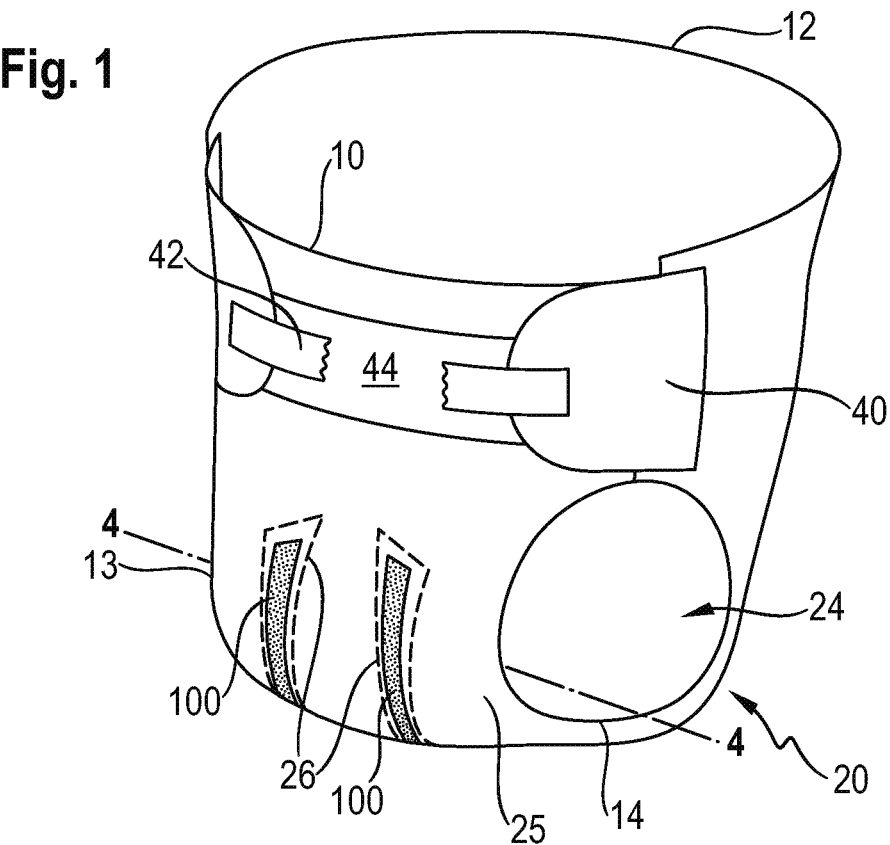
FIG. 1 is a schematic perspective view of an exemplary absorbent article of the invention in the form a taped diaper as it would be worn on the user.

The absorbent article will now be generally discussed and further illustrated in the form of a baby diaper 20 as exemplarily represented in FIG. 1. FIG. 1 is a perspective view of the exemplary diaper 20 as it would be worn by a user (not represented), with the taped back ends 42 attached on the front of the diaper to the landing zone 44. The garment-facing side of the article constitutes its outer-surface when worn by the wearer and essentially consists of a backsheet layer 25. Typical backsheet comprises a liquid-impermeable film, which may be doubled externally by a softer nonwoven layer on its surface. The backsheet film may comprise micro-pores to make the film vapor-permeable. Examples of backsheet layer will be further discussed below.

Figure 3:
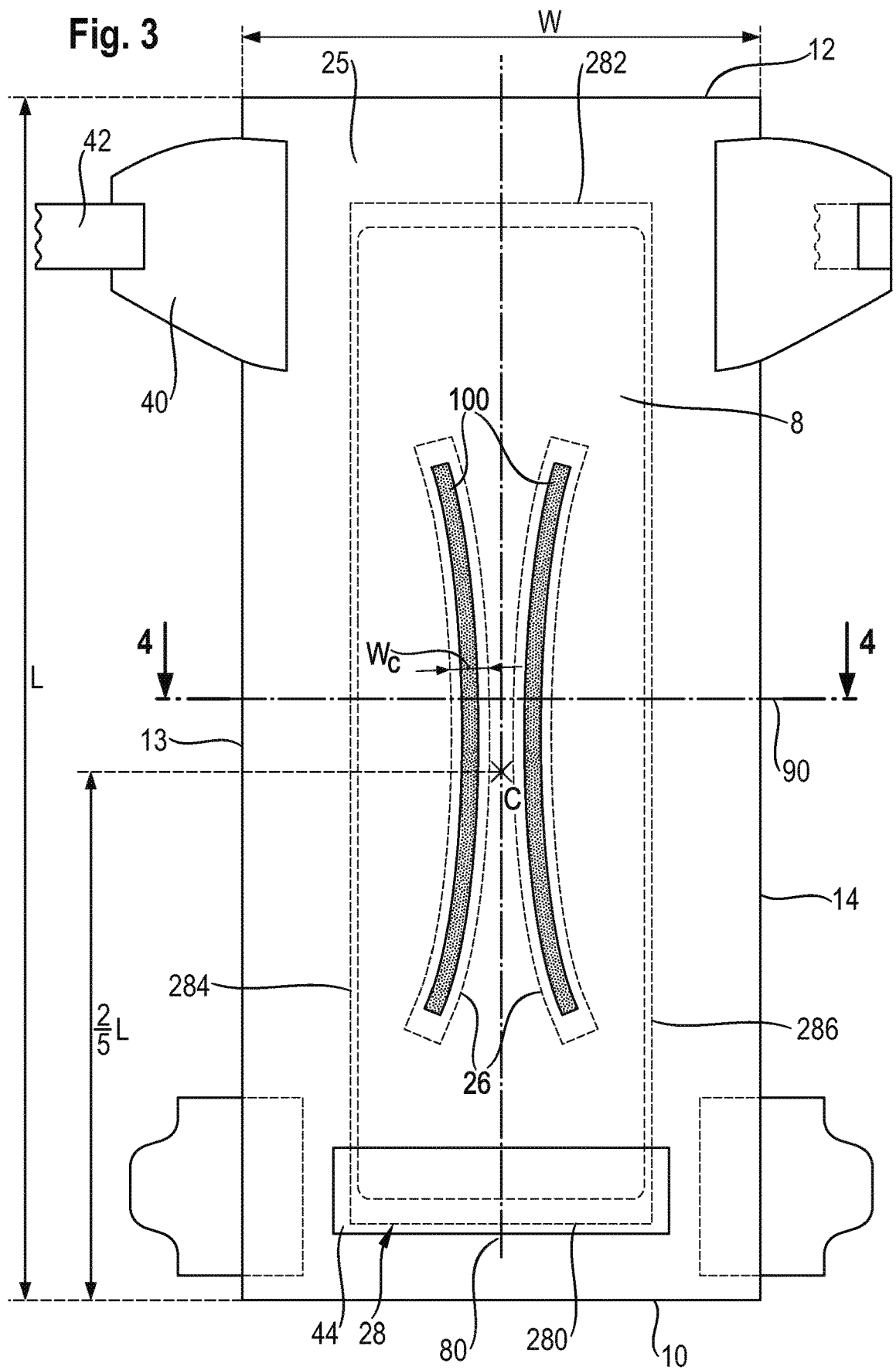
FIG. 3 is a planar view of the garment-facing side of the diaper of FIG. 1 with the article placed flat.

The diaper is further illustrated in a flattened-out configuration with the taped ends opened and the garment-facing side turned up in FIG. 3. An article that is presented to the user closed such as a training pant may also be represented flattened out by cutting it along its side waists. The absorbent article will typically have a front edge 10, a back edge 12 and the longitudinally-extending lateral side edges 13, 14. The front edge 10 forms the edge of the front waist and the back edge 12 of the back waist, which together when worn by the wearer form the opening for the waist of the wearer. The lateral edges 13, 14 can each form one of the leg openings. The article has a longitudinal direction and a transverse direction defined by the longitudinal axis 80 and transversal axis 90 respectively. The longitudinal axis 80 extends through the middle of the front and back edges 10, 12 of the article, and thus virtually divides the article in symmetrical left side and right side. The article has a length L along this longitudinal axis between the front and back edges of the article. The transversal axis 90 extends perpendicularly to the longitudinal axis and crosses the longitudinal axis at a position half way between the front edge and the back edge (L/2 from the front and back edges). The crotch point C of the article is herein defined at the point on the longitudinal axis 80 of the article placed at a distance of ⅖ of L from the front edge.

Figure 2:
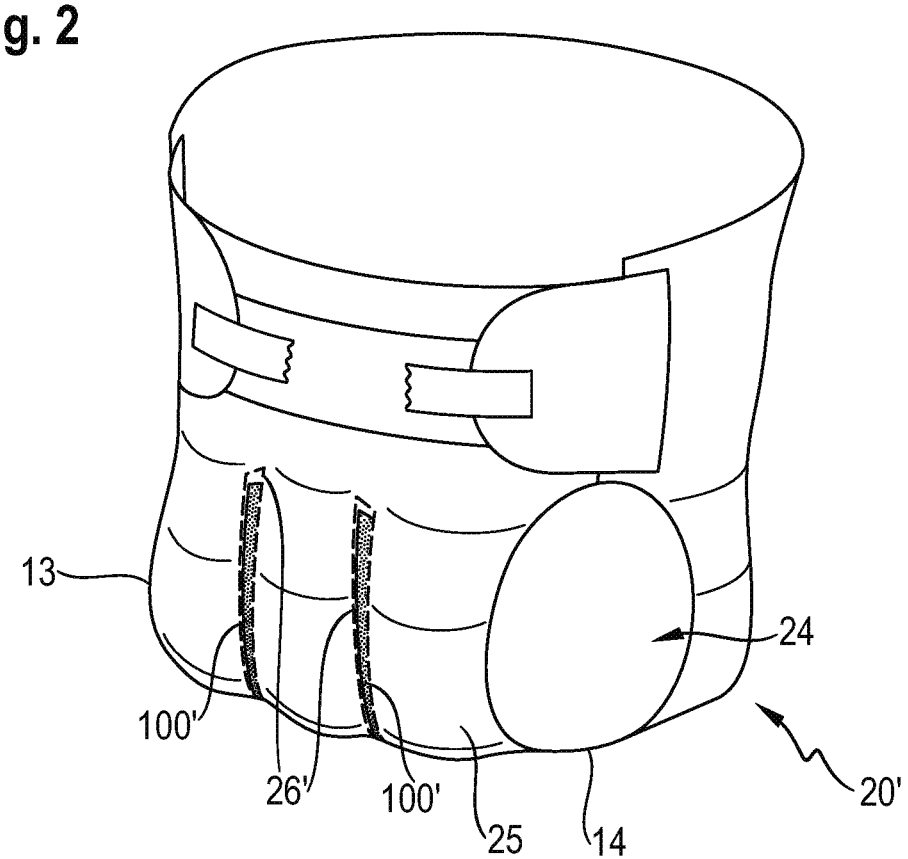
FIG. 2 is a perspective view of the taped diaper of FIG. 1 after it has been loaded with a liquid.
Figure 4:
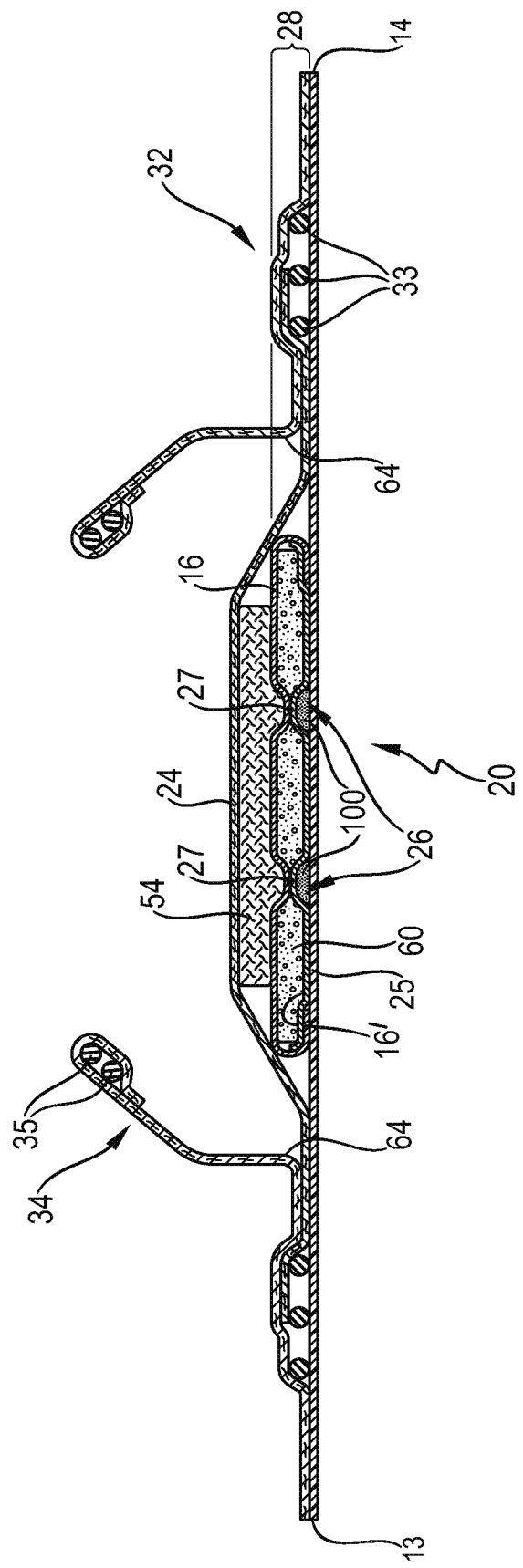
FIG. 4 is a transversal cross-section of the diaper of FIG. 1.

The absorbent articles of the invention comprise at least two generally longitudinally-extending channels 26 in the absorbent core, and at least a wetness indicator 100 visible through the garment-facing area of the article and placed at least partially within the area of the garment-facing side superposed with the channels, as illustrated in FIG. 1 and FIG. 3. When the wearer urinates in the absorbent article, the channels distribute the fluid longitudinally along their length. The wetness indicators which are at least partially superposed with the channels can thus react quicker to a first liquid insult, providing a very early warning to the caregiver that urination has occurred. By "superposed", it is meant that the two elements are positioned in a vertical relation when the article is considered in a flattened configuration as shown in FIGS. 3-4. The superposed components may be in direct or indirect contact. The wetness indicator 100 may typically be a color-change composition as illustrated in FIGS. 1-2, wherein reference 100' designates the reacted wetness indicator having a different appearance (e.g. color) than the un-reacted wetness indicator 100. Similarly, reference 20' designates the article loaded with some fluid such as urine.

Other layers of the absorbent article are better illustrated in FIG. 4, which shows in cross-section in addition to the liquid permeable topsheet 24 and the liquid impermeable backsheet 25, an absorbent core 28 between the topsheet 24 and the backsheet 25. An optional acquisition and/or distribution layer 54 is represented on the diaper of FIG. 4 together with other typical diaper components. Typical acquisition and/or distribution layers 54 do not comprise SAP as this may slow the acquisition and distribution of the fluid, but an additional layer may also comprise SAP if some fluid retention properties are wished. The prior art discloses many type of acquisition and/or distribution layers that may be used, see for example WO2000/59430 (Daley), WO95/10996 (Richards), U.S. Pat. No. 5,700,254 (McDowall), WO02/067809 (Graef).

The absorbent article may typically comprise a pair of partially upstanding barrier leg cuffs 34 and elasticized gasketing cuffs 32 substantially planar with the chassis. Both types of cuffs are typically joined to the chassis of the absorbent article typically via bonding to the topsheet and/or backsheet. U.S. Pat. No. 3,860,003 describes a disposable diaper which provides a contractible leg opening having a side flap and one or more elastic members to provide an elasticized leg cuff (a gasketing cuff 32). U.S. Pat. Nos. 4,808,178 and 4,909,803 issued to Aziz et al. describe disposable diapers having "stand-up" elasticized flaps (barrier leg cuffs 34) which improve the containment of the leg regions. U.S. Pat. Nos. 4,695,278 and 4,795,454 issued to Lawson and to Dragoo respectively, describe disposable diapers having dual cuffs, including gasketing cuffs and barrier leg cuffs. All or a portion of the barrier leg and/or gasketing cuffs may be treated with a lotion. The absorbent article may also comprise other typical components, which are not represented, such as a back elastic waist feature, a front elastic waist feature, transverse barrier cuff(s), a lotion application, etc.

General Description of the Absorbent Core 28

As used herein, the term "absorbent core" refers to a component used or intended to be used in an absorbent article and which comprises an absorbent material enclosed in a core wrap. As used herein, the term "absorbent core" does not include the topsheet, the backsheet and (if present) any acquisition-distribution layer or multilayer system, which is not integral part of the absorbent core. The absorbent core is typically the component of an absorbent article that has the most absorbent capacity of all the components of the absorbent article, and which comprises all, or at least the majority of, superabsorbent polymer (SAP). The absorbent core may consist essentially of, or consist of, the core wrap, the absorbent material and optionally adhesives. The terms "absorbent core" and "core" are herein used interchangeably.

Figure 6:
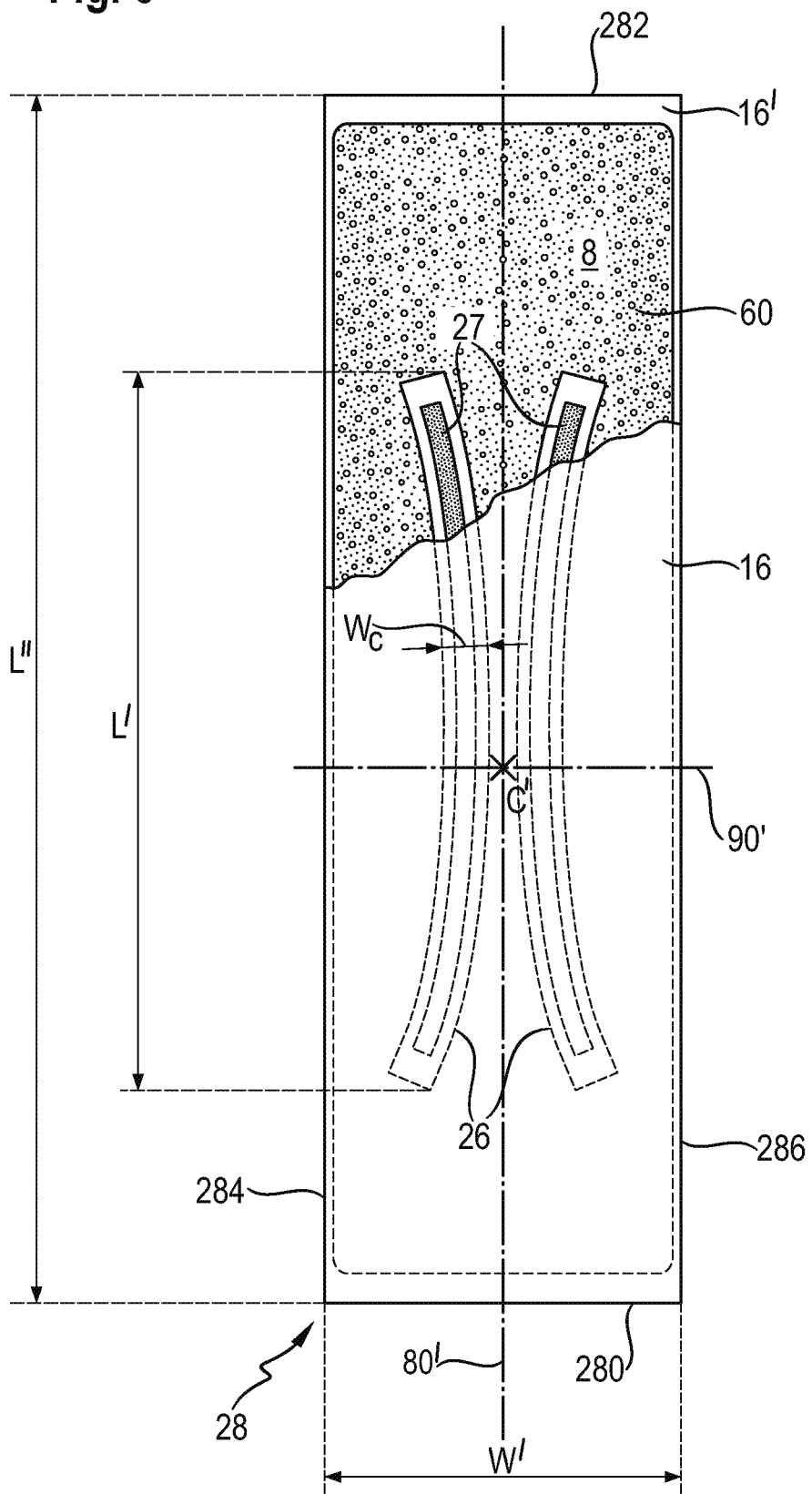
FIG. 6 is a top view of the absorbent core of the article shown in the previous Figures.

An exemplary core 28 comprising channels is represented in FIG. 6 in a dry state outside an absorbent article. Absorbent cores can typically be laid flat on a surface as shown on FIG. 6. Absorbent cores may also be typically thin and conformable, so that they can also be laid on a non-flat surface for example a drum during their making process or stored as a continuous roll of stock material before being converted into an absorbent article. For ease of discussion, the exemplarily absorbent core of FIG. 6 is represented in a flat state and extending in a longitudinal direction 80' and a transversal direction 90'. These directions are typically parallel to the corresponding directions of the absorbent article. Unless otherwise indicated, dimensions and areas disclosed herein apply to the core in this flat-out configuration. The same applies to the absorbent article in which the core is integrated.

The absorbent core can typically be generally rectangular with a width W' in the transversal direction and a length L" in the longitudinal direction as measured from edge to edge, including the region of the core wrap which does not enclose the absorbent material, in particular at the front and back ends 280, 282, which may be or not be sealed. In case the core is not rectangular, the maximum dimension measured along the transversal and longitudinal direction can be used to report the length and width of the core. The width and length of the core may vary depending on the intended usage. For baby and infant diapers, the width W' may for example in the range from 40 mm to 200 mm and the length L" from 100 mm to 500 mm, as measured along the longitudinal axis 80 of the core.

The core wrap may comprise a top layer 16 generally forming the top side of the core and a bottom layer 16' generally forming the bottom side of the core wrap. The top and bottom layers may be formed by two separate substrates which may be the same or different material (the top layer being for example hydrophillically treated), but any other known core wrap constructions may also be used, for example wherein the core wrap is formed of a single web wrapped around the absorbent material with one single longitudinal seal. The top and bottom layer can be attached by gluing or otherwise to form at least one C-wrap seal along each of the longitudinally-extending side edges 284, 286 of the core. The material of the top and bottom layers may be a nonwoven web, such as a laminate comprising spunbond ("S") or meltblown ("M") layer. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US 2011/0268932 A1, US 2011/0319848 A1 and US 2011/0250413 A1. The bottom layer 16' may be inherently hydrophobic but air-permeable, and the top layer 16 may be hydrophillically treated. There may be a seal along the front edge 282 and back edge 280 of the core wrap for better containment of the absorbent material but many cores do not have such transversal seals.

The absorbent material in the core can be of any type, in particular it can comprise wood pulp fibers mixed with superabsorbent polymers or be free of such cellulose fibers ("airfelt-free" core). The first type of core typically comprises from 40% to 80% of superabsorbent polymers (herein abbreviated as "SAP"). For absorbent cores comprising a relatively high proportion of superabsorbent polymer enclosed within the core wrap, the SAP content may represent in particular at least 85%, 90%, 95% and up to 100%, of superabsorbent polymer by weight of the absorbent material. The absorbent material may in particular comprise no or only small amount of cellulose fibers, such as less than 20%, in particular less than 10%, 5% or even 0% of cellulose fibers by weight of the absorbent material. The absorbent material may thus advantageously consist or consist essentially of SAP. The term "superabsorbent polymer" refers herein to absorbent material, which may be cross-linked polymer, and that can typically absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 20 to 40 g/g, or from 24 to 30 g/g. The SAP may be typically in particulate forms (superabsorbent polymer particles), but it not excluded that other forms of SAP may be used such as a superabsorbent polymer foam for example. The absorbent core may thus be relatively thin, in particular thinner than conventional cores comprising cellulosic fibers.

Figure 7:
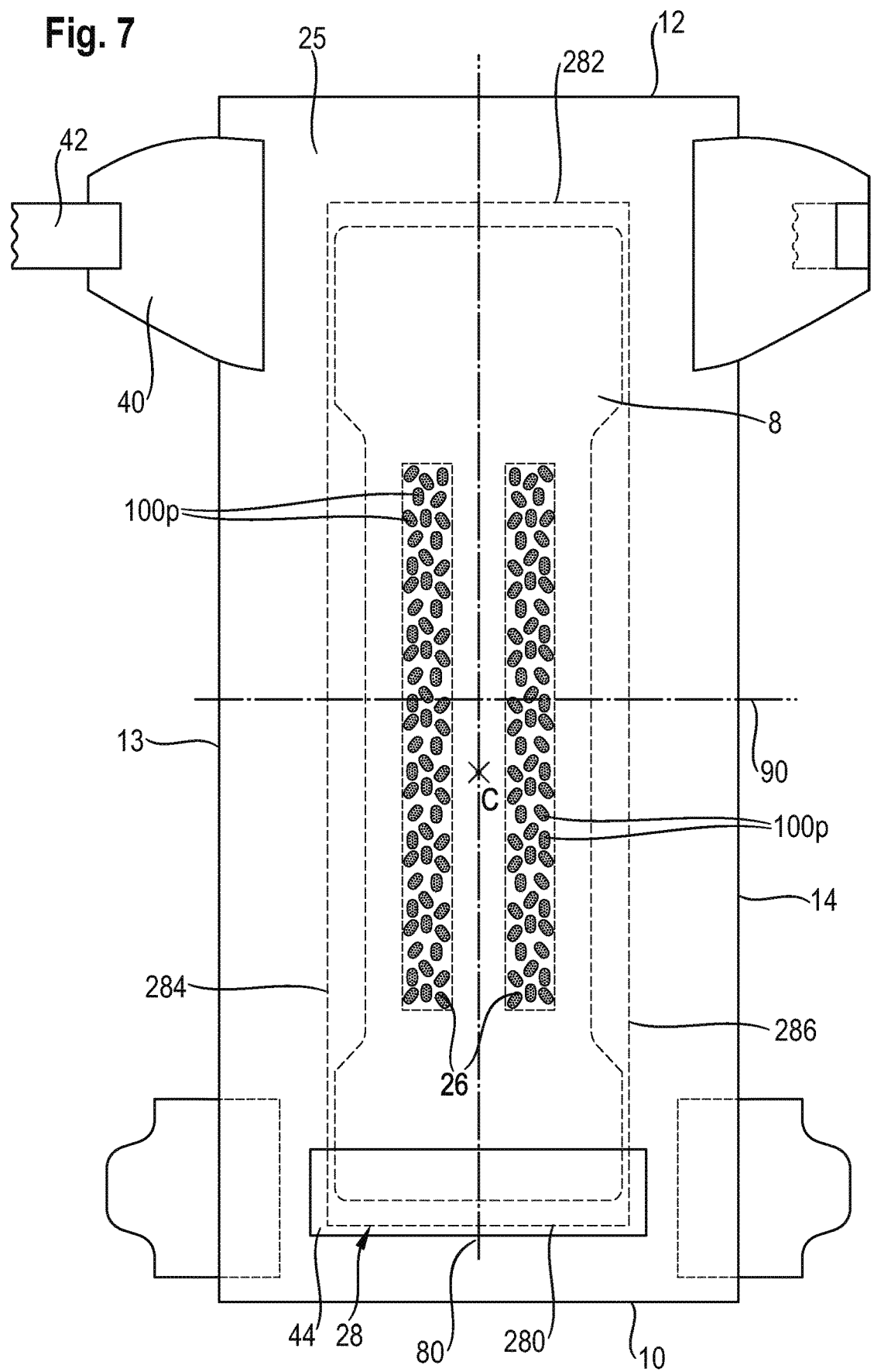
FIG. 7 is a planar view of the garment-facing side of an alternative article.

The absorbent material 60 defines an absorbent material deposition area 8, as seen from above within the plane of the core from the top side of the absorbent core as shown on FIG. 6. The deposition area comprises the channels 26 encompassed within. The absorbent material deposition area 8 can be generally rectangular, for example as shown in FIG. 6, but other shapes can also be used such as a "T" or "Y" or "sand-hour" or "dog-bone" shape. In particular the deposition area may show a tapering along its width at the crotch region of the core, as illustrated in FIG. 7. In this way, the absorbent material deposition area may have a relatively narrow width in an area of the core intended to be placed in the crotch region of the absorbent article. This may provide for example better wearing comfort.

Channels 26

The absorbent cores of the invention comprise a pair of generally longitudinally-extending channels 26 symmetrically disposed relative to the longitudinal axis 80 of the absorbent article. The channels may be provided by various means as is known in the art. Typically, channels may be formed by areas within the absorbent core that are substantially free of absorbent material (as illustrated in FIG. 4 and FIG. 6). By "substantially free" it is meant that in the channel areas the basis weight of the absorbent material is at least less than 25%, in particular at least less than 20% or less than 10%, of the average basis weight of the absorbent material in the rest of the absorbent material deposition area 8. In particular there can be no absorbent material in the channels. Minimal amount such as involuntary contaminations with absorbent material that may occur during the making process are not considered as absorbent material. The channels 26 are advantageously surrounded by the absorbent material, when seen in the plane of the core as seen on FIG. 6, which means that the channels do not extend to any of the edge of the deposition area 8 of the absorbent material.

Figure 5:
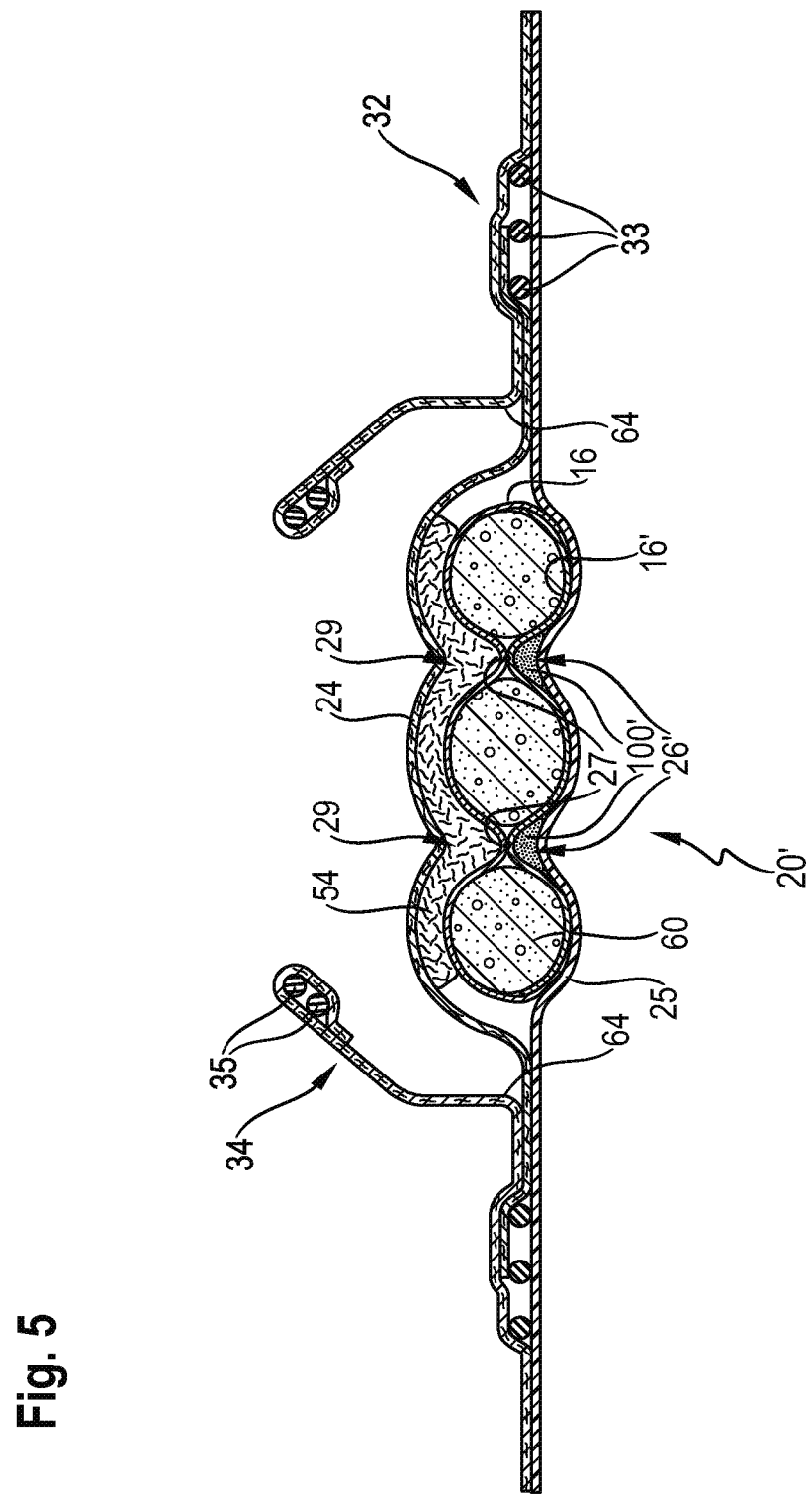
FIG. 5 is a transversal cross-section of the article taken at the same point as FIG. 4, wherein the absorbent material has swollen as a result of being loaded with a liquid such as urine.

The top layer 16 of the core wrap may be attached to the bottom layer 16' of the core wrap by core wrap bonds 27 through the channels 26 as illustrated in FIG. 4. As shown in FIGS. 4-5, when the absorbent material swells upon absorbing a liquid, the core wrap bond 27 may thus remain at least initially attached in the channels 26. The absorbent material swells in the rest of the core when it absorbs a liquid, so that the core wrap forms three-dimensional channels 26' along each channel 26 where the core wrap bond 27 is present. The initial channels 26 and the three-dimensional channels 26' can distribute an insulting fluid along their length to a wider area of the core and thus provide a quicker fluid acquisition speed and a better utilization of the absorbent capacity of the core. As the absorbent material swells, the channels 26' become deeper and deep enough (a depth of several mm, e.g. at least 3 mm, as measured on the swollen core) to be visible from the exterior of the article through the backsheet. The three-dimensional channels 26' can also provide a deformation of an overlying layer such as a fibrous layer 54 and provide corresponding ditches 29 in the overlying layer. Channels may also be formed in an absorbent core by area(s) substantially free of absorbent material, but without a core wrap bond. The non-bonded channels will typically form less pronounced three-dimensional channels when wet compared to bonded channels.

When present, the core wrap bond 27 may be continuously extending along the channels 26, but it may also be discontinuous (intermittent) such as series of point bonds. Typically, an adhesive can be used to attach the top layer to the bottom layer of the core wrap through the channels, but it is also possible to bond via other known attachment means, such as pressure bonding, ultrasonic bonding or heat bonding or combination thereof. The core wrap bond may be provided by one or more adhesive material, in particular one or more layers of auxiliary glue (not represented) or layer of fibrous adhesive material, if present in the core, as detailed below. These glues may therefore serve the dual function of immobilizing the absorbent material and attach the top layer and the bottom layer of the core together. The auxiliary glue(s) may be applied by slot coating in a series of thin (e.g. 1 mm wide) glue slots in the longitudinal direction.

The following are examples of shape and size of channels, but are not limiting the scope of the invention. In general, the core wrap bond 27 may have the same outline but be slightly smaller than the channels 26 due to the tolerance required in some manufacturing process. The channels 26 may be present within the crotch region of the article, as defined as being the longitudinally middle third of the article. The absorbent core may also comprise more than two channels, for example at least 3, or at least 4 or at least 5 or at least 6.

The channels 26 extend generally longitudinally, which means that each channel area extends at least as much in the longitudinal direction as in the transverse direction, and typically at least twice as much in the longitudinal direction than in the transverse direction (as measured after projection on the respective axis). The absorbent core, as illustrated in FIG. 6, typically also have a longitudinal axis 80' which is contiguous with the longitudinal axis of the article. The channels 26 may have a length L' projected on the longitudinal axis 80' of the core that is at least 10% of the length L of the absorbent article, in particular from 20% to 80%. The channels 26 may be for example have a length L' of at least 2 cm as measured on the longitudinal axis, or at least 4 cm, 6 cm, 8 cm, or 10 cm, and for example up to 40 cm, or 30 cm. Shorter channels may also be present in the core, for example in the back region or the front region of the core, as seen for example in the Figures of WO2012/170778.

The channels 26 comprise or may consist of a pair of channels symmetrically arranged relative to the longitudinal axis 80 of the article as illustrated by way of example in the Figures. The channels 26 may be curved, in particular they may be concave towards the longitudinal axis 80/80', as for example represented in FIGS. 3 and 6, or they may be completely oriented longitudinally and parallel to the longitudinal axis 80' of the core as illustrated in FIG. 7. For curved channels, the radius of curvature may typically be at least equal (and preferably at least 1.5 or at least 2.0 times this average transverse dimension) to the average transverse dimension of the absorbent material deposition area 8. The channels may be entirely or in part straight but under an angle of (e.g. from) 5° up to 30°, or for example up to 20°, or up to 10° with a line parallel to the longitudinal axis. The radius of curvature may be constant for a channel, or may vary along its length. It is further advantageous that there is no channel superposed or coinciding with the longitudinal axis 80 of the article to avoid the article from folding in this direction. The channels may be advantageously spaced apart from one another over their whole longitudinal dimension. The smallest spacing distance may be for example at least 5 mm, or at least 10 mm, or at least 16 mm, leaving sufficient space there between for the wetness indicator.

Furthermore, in order to reduce the risk of fluid leakages, the channels 26 may advantageously not extend up to any of the edges of the absorbent material deposition area 8, and are therefore surrounded by and fully encompassed within the absorbent material deposition area 8 of the core. Typically, the smallest distance between a channel 26 and the closest edge of the absorbent material deposition area 8 is at least 5 mm. Each channel may have a width Wc along at least part of its length which is at least 2 mm, or at least 3 mm or at least 4 mm, up to for example 20 mm, or 16 mm or 12 mm. The width Wc of each channel 26 may be constant through substantially its whole length or may vary along its length.

Three-dimensional channels 26' in the absorbent core start forming when the absorbent material absorbs a liquid such as urine and starts swelling. As the core absorbs more liquid, the depressions formed by these channels will become deeper and more apparent to the eye and the touch from the exterior of the article as the backsheet is pushed outwardly by the expending absorbent material, as illustrated in FIGS. 2 and 5. If the core wrap bond 27 is sufficiently strong and the level of SAP not too high, it is possible that the core wrap bonds remain permanent until complete saturation of the absorbent material. On the other hand, the core wrap bonds may in some cases also restrict the swelling of the absorbent material when the core is substantially loaded. The inventors have thus found that the core wrap bond 27 may also be designed to open in a controlled manner when exposed to a large amount of fluid. The bonds may thus remain substantially intact at least during a first phase as the absorbent material absorbs a moderate quantity of fluid. In a second phase the core wrap bonds 27 in the channels can start opening to provide more space for the absorbent material to swell while keeping most of the benefits of the channels such as increased flexibility of the core in transversal direction and fluid management. In a third phase, corresponding to a very high saturation of the absorbent core, a more substantial part of the channel bonds can open to provide even more space for the swelling absorbent material to expand. The strength of core wrap bond 27 within the channels can be controlled for example by varying the amount and nature of the glue used for the attaching the two sides of the core wrap, the pressure used to make the core wrap bond and/or the distribution of the absorbent material, as more absorbent material will usually cause more swelling and will put more pressure on the bond. The extensibility of the material of the core wrap may also play a role.

Wetness Indicator 100

The absorbent article 20 comprises a wetness indicator 100 which is visible from the garment-facing side of the article and which changes appearance when contacted with a body exudates, in particular urine. The wetness indicator may comprise a single area but it also may comprise several areas. For example, when the absorbent article comprises two channels, the absorbent article may comprise the wetness indicator in two areas, one for each channel. Within one channel area, the wetness indicator may also comprise a single area as illustrated in FIG. 3, but it is also possible that the wetness indicator may be comprised by a plurality of wetness indicator areas 100p as illustrated in FIG. 7. The latter may allow printing more aesthetically pleasing pattern for example with animal shapes, geometrical shapes such as triangle, square or circles, or object shapes like toys, cars, etc. Herein, the term "wetness indicator" will thus be used independently of the numbers of discrete wetness indicator areas present and visible through the garment-facing side.

The wetness indicator 100 is at least partially superposed with the areas defined by the channels, when seen from the garment-facing side as in FIG. 3. By "superposed", it is meant that the wetness indicator is at least partially positioned vertically congruent in the areas defined by the channels, when the article is considered in a flattened configuration as shown in FIGS. 3-4. By "as seen from the garment-facing side of the article", it is meant that although the wetness indicator 100 may not be placed directly in the plane of the channels 26 or even within the core 28, when considering the article 20 from the outside, that is typically looking at the outward surface of the backsheet as shown on FIG. 1, the wetness indicator appears at least partially placed within the channels 26. As the three-dimensional channels 26' are typically visible from the outside of the article when the article is sufficiently loaded with urine, as shown in FIG. 2, the wetness indicator also typically appears placed within the three-dimensional channels 26' in the loaded article when seen from the exterior of the article. The word "seems" should be construed herein in a broad sense, as in some embodiments, the wetness indicator may comprise or consists of an appearing signal or a disappearing signal, so that the wetness indicator is only visible to an observer in the wet or dry state, as will be exemplified further below. This arrangement according to the invention provides for a quicker reaction of the wetness indicator to an insulting fluid. The wetness indicator also serves to indicate the position of the channels to the user of the article. The channels 26 may otherwise not be immediately recognizable in a dry article. The wetness indicator may be further typically placed between the backsheet and the absorbent core, i.e. between the bottom layer of the core wrap of the absorbent core and the backsheet, typically the polymeric film layer that constitutes at least part of the backsheet.

The wetness indicators of the present invention may be according to any wetness indicating system known in the art. It is known that wetness indicator can provide an appearing signal, a disappearing signal or a color change signal, and of course combinations thereof. Typically, a color change signal will be used, examples of which will be more detailed below.

An appearing signal will typically not be visible or more generally perceivable in the dry article, and becomes visible or otherwise perceivable when the article is wet. An appearing signal may for example be provided by a composition which is transparent or having a color that matches the color of the backsheet material, which is typically white, in its dry state, and then changes to a different color when contacted with urine. Other appearing wetness indicator may also be elements capable of providing a physical sensation indicating a fullness level of the absorbent assembly. Examples of such elements are disclosed in WO2008/132630 and include a temperature change element (cooling or heating element), a pressure-inducing element or a foam-producing element.

The wetness indicator may provide a disappearing signal when the article is wet. A disappearing signal may be provided by a composition that a first color when dry and which changes to a second color that matches the general color of the backsheet or any graphic printed on the backsheet, so that the second color is less discernible that the first color on the article. Such a disappearing signal may be provided for example by a composition comprising a dye that dissolves in urine and thus fades as the article is wetted.

The wetness indicator may advantageously provide a color change signal, which may be typically obtained by a composition having a first color when dry and a second color different form the first color when wet, both colors being discernible by an external observer considering the article in a dry and a wet state. The wetness indicator may in particular be a color change composition comprising a suitable pH indicator or another chemical substance that changes color when contacted with urine. Such compositions are for example disclosed in WO03/070138A2, WO2010/120705 (Klofta) or US2012/165771 (Ruman). The documents cited previously give several examples of such suitable pH indicator, which for example include bromocresol green, bromocresol purple, bromophenol blue, m-cresol purple, cresol red, chlorophenol red, bromothymol blue, bromopyrogallol red, bromoxylenol blue, acridine, or acridine orange, thymolphthalein, thymol blue, xylenol blue, bromochlorophenol blue and indigo carmine. Bromocresol green for example may be applied in a composition having an acid stabilizer so that the pH indicator appears yellow on a dry article and turns to a green-blue shade when contacted with urine, the typical pH of urine being around pH 7.

More generally, the wetness indicator compositions of the invention may be as disclosed in WO2010/120705 (Klofta) and comprises a colorant, a matrix and a stabilizer. The colorant has an initial color state, which is associated with a first state of the wetness indicator composition. Examples of this first color state include, but are not limited to, colors visible to the human eye, such as, red, blue, green, indigo, violet, yellow, orange, purple, and the like; colors not visible to the human eye, such as, colors visible in the ultra violet (or UV), or infra red (or IR) portion of the electromagnetic spectrum, and the like. The first color state may be invisible, white, black, translucent or opaque. The colorant(s) also has a final color state, which is associated with a second state of the wetness indicator composition. Examples of this second color state include, but are not limited to, colors visible to the human eye, such as, red, blue, green, indigo, violet, yellow, orange, purple, and the like; colors not visible to the human eye, such as, colors visible in the UV, or IR portion of the electromagnetic spectrum, and the like. The second color state may be invisible, white, black, translucent, opaque, or have a change in intensity or visual distinctiveness, and the like, when compared to the first color state. The initial color state of the colorant is different, in some form, to the final color state. For example, the initial color state may be a first color, such as yellow, while the second color state may be a different color, such as blue; or the initial color state may be a first color, such as blue, while the second color state may be transparent, such as a color not visible to the human eye, and only visible in the UV portion of the electromagnetic spectrum. In an optional embodiment of the present invention the wetness indicator composition may comprise two or more colorants. The colorant may be employed in compositions at levels which are effective at indicating the presence of a liquid, and include from about 0.001% to about 5%, from about 0.005% to about 2%, and from about 0.01% to about 1%, and even from 0.01% to 0.5% by weight of the composition.

The wetness indicator compositions may comprise a matrix which acts to hold the colorant in place before, during and after contact with liquid. The matrix of the present invention may be highly resistant to colorant leaching, and may be resistant to premature activation in high humidity environments. Upon contact with liquid, such as urine, menses, blood or the like, the matrix allows sufficient liquid to contact the colorant and effect a change in appearance. The matrix concurrently aids in inhibiting the colorant, in either its initial color state or final color state, from leaching out of the matrix into the surrounding environment, such as, the absorbent core of a disposable absorbent article. When the wetness indicating composition is attached to a substrate, the matrix and consequently the composition, should have sufficient wet and dry cohesion, adhesion, and/or flexibility to remain fully retained on the substrate. Such a matrix may include a first and second binding agents, as disclosed in details in WO2010/120705 and may be employed in wetness indicator compositions at levels which are effective at immobilizing and stabilizing the colorant, including from about 5% to about 95%, from about 10% to about 80%, and from about 25% to about 75%, by weight of the composition.

The first binding agent may be any material which immobilizes the colorant when the colorant is in its initial color state. There are various materials which may be suitable for use as the first binding agent for the wetness indicating compositions of the present invention. The material selected as the first binding agent will be any material which immobilizes the colorant when in its first color state. Possible first binding agents include, but are not limited to, rosins, rosin esters, polymerized rosins, pentaerythritol rosin esters, styrenated terpenes, polyterpene resins, terpene phenolics, and combinations thereof. The first binding agent may be employed in compositions at levels which are effective at immobilizing and stabilizing the colorant in its first state, including from about 4% to about 90%, from about 10% to about 75%, and from about 20% to about 65%, by weight of the composition.

The second binding agent may be any material which immobilizes the colorant when the colorant is in its final color state. There are various materials which may be suitable for use as the second binding agent for the wetness indicating compositions of the present invention. The second binding agents may be selected from, but are not limited to those second binding agents disclosed in U.S. Pat. No. 6,904,865 to Klofta. The second binding agent may be selected from the group consisting of quaternary ammonium salt compounds, cationic clay, polyacrylic acid polymers, organic acids, and combinations thereof. Examples of suitable quaternary ammonium compounds include, but are not limited to, dimethyl(2-ethylhexylhydrogenatedtallowalkyl) ammonium methyl sulfate, cocoalkylmethyl[ethoxylated (15)] ammonium chloride, dodecyltrimethyl ammonium chloride, hexadecyltrimethyl ammonium methyl sulfate, octadecyltrimethyl ammonium chloride, dicocoalkyldimethly ammonium chloride, di(hydrogenated tallowalkyl)dimethyl ammonium chloride, and distearyldimethyl ammonium chloride. It should be noted that the counter anion associated with the quaternary compound, or any second binding agent having one or more cationic group, is not specifically limited to chloride. Other anions can also be employed and non-limiting examples include methyl sulfate and nitrite. Similarly, any suitable counter cation, such as, but not limited to, sodium, potassium, calcium, magnesium, zinc, protons, ammonium, substituted ammonium and the like, may be associated with a second binding agent having one or more anionic groups.

Wetness indicator compositions may further include a stabilizer, as detailed e.g. in WO2010/120705. It may be desirable to include a stabilizer when the colorant is a pH indicator and when the absorbent article could be stored under conditions of high humidities and temperatures. The inclusion of a stabilizer within the wetness indicator composition is also especially important for new diaper designs where materials and/or chemicals are present that could potentially prematurely activate the color change of the colorant within the wetness indicator composition. The stabilizer may be an acidic or a basic stabilizer. The inclusion of a stabilizer, while not wishing to be limited by theory, is believed to play a role in stabilizing the colorant against premature changes caused by exposure to humid environments and/or certain components of the diaper, by maintaining a stable pH, such as a low pH environment with an acidic stabilizer, around the colorant even when the system is exposed to high humidities and/or certain components of the diaper. This maintenance of a stable pH environment keeps the colorant, especially when the colorant is a pH indicator, in its initial dry color state. The stabilizer, when present is typically employed in compositions at levels which are effective at stabilizing the colorant, from about 0.001% to about 30%, from about 0.1% to about 15%, and also from about 1% to about 10%, by weight of the composition.

The color change composition may further be a hot-melt adhesive, which allows for an easy application of the composition on a substrate component of the article for example by a slot coating process, inkjet printing or in particular printed adhesive coating, as for example disclosed in US2011/274834 (Brown). A printed adhesive coating allows in particular the precise placement of a hotmelt composition comprising a wetness indicator agent in selected areas of a substrate such as the inwardly facing surface of the backsheet layer of the article. U.S. Pat. No. 8,186,296 (Brown) discloses an apparatuses that can be used to apply viscous fluids, such as adhesives comprising a color change agent, in pre-determined patterns to an advancing substrate. The fluid application apparatus may include a slot die applicator and a substrate carrier. The substrate carrier may include one or more pattern elements and may be adapted to advance the substrate past the slot die applicator as the slot die applicator discharges adhesive onto the substrate. In operation, the substrate is disposed on the substrate carrier; the substrate carrier advances the substrate past the slot opening of the slot die applicator. In turn, the substrate is intermittently compressed between the slot die applicator and the pattern surface of the pattern element. As the substrate is intermittently compressed, adhesive discharged from the slot die applicator is applied onto the substrate in an area having a shape substantially the same as a shape defined by the pattern surface.

A hot melt adhesive composition may typically become fluid at a temperature of above 60° C. and solidifies when it touches the substrate on which it is applied as it cools down. Hot-melt adhesives may include one or more polymers to provide cohesive strength (e.g., aliphatic polyolefins such as ethylene-propylene copolymers, polyetheramides, polyetheresters, and combinations thereof; ethylene vinyl acetate copolymers; styrene-butadiene or styrene-isoprene block copolymers; etc.), a resin or analogous material (sometimes called a tackifier) to provide adhesive strength (e.g., hydrocarbons distilled from petroleum distillates; rosins and/or rosin esters; terpenes derived, for example, from wood or citrus, etc.); and optional waxes, plasticizers or other materials to modify viscosity (e.g., mineral oil, polybutene, paraffin oils, ester oils, and the like), and/or other additives including, but not limited to, antioxidants or other stabilizers. The matrix may comprise a first and a second binding agent. The matrix acts to hold the colorant in place before, during and after contact with liquid.

More generally, hot-melt wetness indicators of the invention (HMWI) may comprise a pH sensitive colorant (pH Indicator), a water insoluble component (resin/tackifier), a wetting agent (polymer, surfactant), a stabilizing agent (acid), a rheology modifier and anti-oxidants for example in the following range in weight percent:

| | |
|---|---|
| pH Indicator (e.g. Bromocresol green) | <0.5 |
| Tackifier | 25-45 |
| Surfactant | 10-20 |
| Water-soluble polymer | 00-10 |
| Fatty acids | 30-50 |
| Plasticizer | 00-10 |

Figure 8:
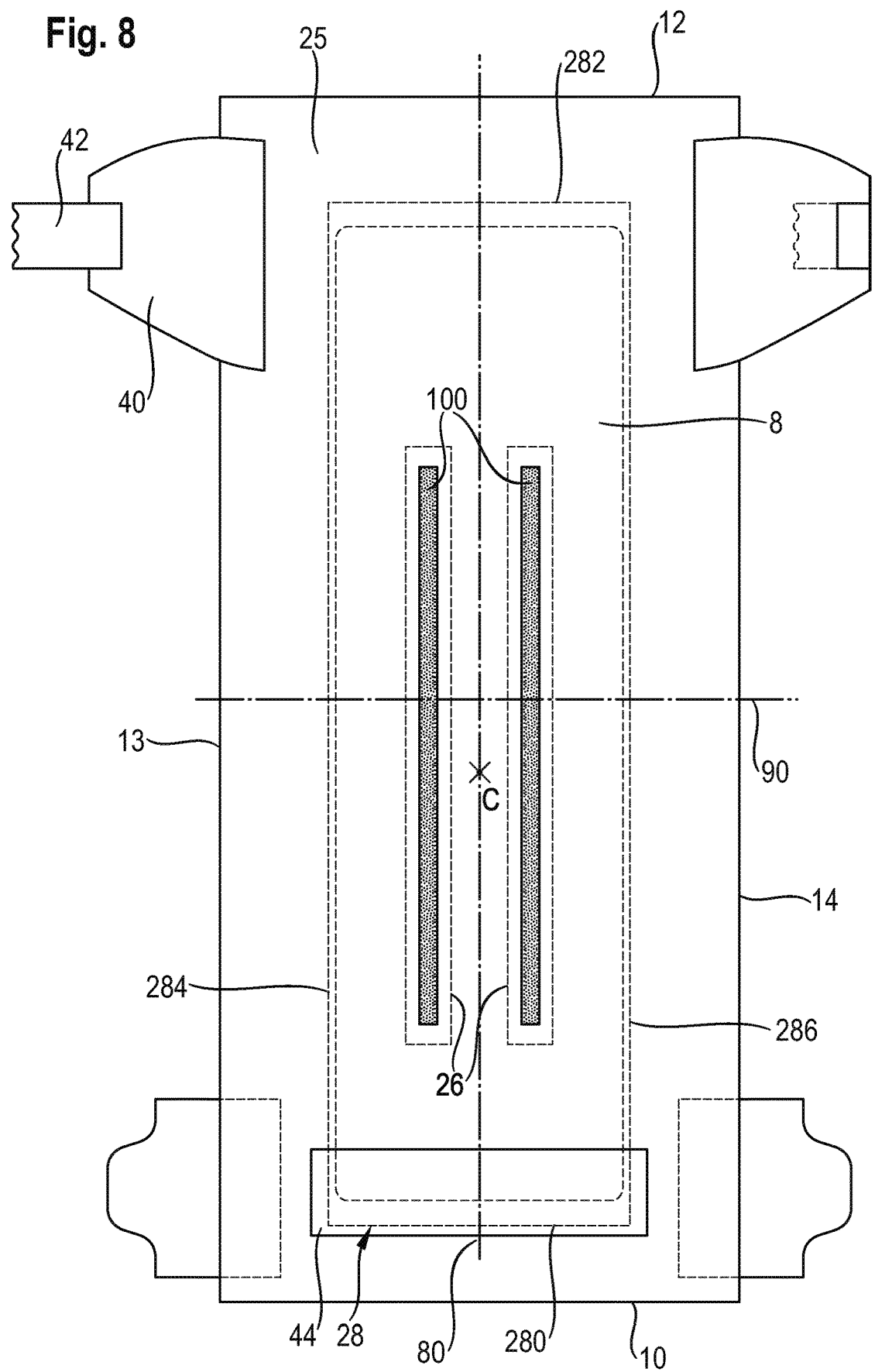
FIG. 8 is a planar view of the garment-facing side of another alternative article.

The wetness indicator composition may be applied on any layer of the absorbent article using a conventional technique, for example printing, spraying or coating, or printed adhesive coating as indicated previously, during the making of the absorbent article. The layer may advantageously be the inner surface of the backsheet or the outer surface of the bottom layer of the core wrap. This allows the wetness indicator to be visible from the exterior of the article by transparency through the backsheet while keeping the wetness indicator composition within the article. The wetness indicator may in particular be easily applied on a layer such a nonwoven or film by a slot-coating process especially if the composition is can be applied as a hot-melt. The slot-coating process allows applying a well-defined slot or a series of slots extending in the machine direction of the converting line, which is typically parallel to the longitudinal direction of the article. Such a slot 100 of wetness indicator composition is for example shown on FIG. 8, in the form of the two longitudinally extending wetness indicator areas 100, each present within an equally longitudinally extending channel 26.

The wetness indicator may be smaller, longer, thinner, wider or of an equal length or width than each of the channels 26 where it is present. It may be typically advantageous to have a relatively long wetness indicator, for example at least 10 cm long, so as to give to the caregiver a better indication of the amount or repartition of the fluid in the article. The wetness indicator may be entirely encompassed in the area of defined by the channels 26 as shown in the Figures, but it is also not excluded that the wetness indicator may be partially situated outside the channels.

Method of Making the Article—Relations Between the Layers

The absorbent articles of the invention may be made by any conventional methods known in the art. In particular the articles may be hand-made or industrially produced at high speed. Typically, adjacent layers and components will be joined together using conventional bonding method such as adhesive coating via slot coating or spraying on the whole or part of the surface of the layer, or thermo-bonding, or pressure bonding or combinations thereof. This bonding is exemplarily represented for the bond 27 between the core wrap layers within the channels 26. Other glues or attachments are not represented for clarity and readability but typical bonding between the layers of the article should be considered to be present unless specifically excluded. Adhesives may be typically used to improve the adhesion of the different layers, for example between the backsheet and the core wrap. The glues used may be any standard hotmelt glue as known in the art.

The absorbent core 28 and in particular its absorbent material deposition area 8 may or may not be at least as large and long and advantageously at least partially larger and/or longer than a fibrous acquisition and/or distribution layer 54. This is because the absorbent material in the core can usually more effectively retain fluid and provide dryness benefits across a larger area than the fibrous layer 54. The absorbent article may have a rectangular SAP layer and a non-rectangular (shaped) fibrous acquisition/distribution layer. The absorbent article may also have a rectangular (non-shaped) fibrous layer and a rectangular layer of SAP.

MISC

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, having a wearer-facing side and a garment-facing side and a longitudinal axis; the absorbent article comprising:
   a topsheet on the wearer-facing side,
   a backsheet on the garment-facing side, and
   an absorbent core between the topsheet and backsheet;
   the absorbent core comprising a core wrap having a
      hydrophilic top layer and a hydrophobic bottom layer enclosing an absorbent material, wherein the absorbent core comprises a generally longitudinally-extending channel;

wherein the absorbent article further comprises a wetness indicator having a water soluble dye, wherein the wetness indicator is at least partially superposed over the channel, as seen from the garment-facing side of the article, and wherein the wetness indicator is disposed between the backsheet and the absorbent core.

2. The absorbent article according to claim 1, wherein the wetness indicator comprises a width that is thinner or equal to a width of the channel.

3. The absorbent article of claim 1, wherein the wetness indicator comprises a composition disposed on the backsheet, wherein the composition becomes visible from the garment-facing side of the article when contacted with urine.

4. The absorbent article of claim 1, wherein the wetness indicator comprises a single wetness indicator area in the channel where the wetness indicator is present.

5. The absorbent article of claim 1, wherein the wetness indicator comprises two or more wetness indicator areas.

6. The absorbent article of claim 1, wherein the absorbent core does not comprise a channel superposed with the longitudinal axis.

7. The absorbent article of claim 1, wherein the channel is an area of the absorbent core substantially free of the absorbent material.

8. The absorbent article of claim 1, wherein the top layer of the core wrap is bonded to the bottom layer of the core wrap through the channel.

9. The absorbent article according to claim 1, wherein the absorbent material comprises from 40% to 80% of superabsorbent polymer particles by weight of the absorbent material.

10. The absorbent article of claim 9, wherein the absorbent material comprises at least 70% of superabsorbent polymer particles by weight of the absorbent material.

11. The absorbent article of claim 1, wherein the channel comprises a curvilinear portion.

12. The absorbent article of claim 1, wherein a portion of the channel has a width (Wc) of at least 2 mm.

13. The absorbent article of claim 1, wherein the wetness indicator provides an appearing signal, a disappearing signal, a color change signal or a combination thereof.

14. An absorbent article, having a wearer-facing side and a garment-facing side and a longitudinal axis; the absorbent article comprising:

a topsheet on the wearer-facing side,
a backsheet on the garment-facing side, and
an absorbent core between the topsheet and backsheet;
the absorbent core comprising a core wrap having a hydrophilic top layer and a hydrophobic bottom layer enclosing an absorbent material disposed in an absorbent material deposition area, wherein the absorbent core comprises a generally longitudinally-extending channel;
wherein the absorbent article further comprises a wetness indicator at least partially superposed with the channel, as seen from the garment-facing side of the article, and
wherein the wetness indicator comprises a hot melt adhesive.

15. The absorbent article of claim 14, wherein the channel comprises a curvilinear portion.

16. The absorbent article of claim 14, wherein a portion of the channel has a width (Wc) of at least 2 mm.

17. The absorbent article of claim 14, wherein the wetness indicator provides an appearing signal, a disappearing signal, a color change signal or a combination thereof.

18. The absorbent article of claim 14, wherein the absorbent core does not comprise a channel superposed with the longitudinal axis.

19. The absorbent article of claim 14, wherein the channel is an area of the absorbent core substantially free of the absorbent material.

20. An absorbent article, having a wearer-facing side and a garment-facing side and a longitudinal axis; the absorbent article comprising:

a topsheet on the wearer-facing side,
a backsheet on the garment-facing side, and
an absorbent core between the topsheet and backsheet;
the absorbent core comprising a core wrap having a hydrophilic top layer and a hydrophobic bottom layer enclosing an absorbent material disposed in an absorbent material deposition area,
wherein the absorbent core comprises a generally longitudinally-extending channel;
wherein the absorbent article further comprises a wetness indicator at least partially superposed with the channel, as seen from the garment-facing side of the article,
wherein the wetness indicator comprises a width that is thinner or equal to a width of the channel at a given longitudinal position.

* * * * *